US012698314B2

(12) United States Patent
Brennan et al.

(10) Patent No.: US 12,698,314 B2
(45) Date of Patent: Aug. 4, 2026

(54) EXTENDED TIME ACTION ACYLATED INSULIN COMPOUNDS

(71) Applicant: Eli Lilly and Company, Indianapolis, IN (US)

(72) Inventors: Seamus Patrick Brennan, Indianapolis, IN (US); David Benjamin Flora, Greenfield, IN (US); Vladislav Kisselev, Carmel, IN (US); Wen Liu, Carmel, IN (US); Francisco Alcides Valenzuela, Indianapolis, IN (US)

(73) Assignee: Eli Lilly and Company, Indianapolis, IN (US)

( * ) Notice: Subject to any disclaimer, the term of this patent is extended or adjusted under 35 U.S.C. 154(b) by 803 days.

(21) Appl. No.: 17/998,090

(22) PCT Filed: May 13, 2021

(86) PCT No.: PCT/US2021/032144

§ 371 (c)(1),
(2) Date: Nov. 7, 2022

(87) PCT Pub. No.: WO2021/231676

PCT Pub. Date: Nov. 18, 2021

(65) Prior Publication Data

US 2023/0174609 A1 Jun. 8, 2023

Related U.S. Application Data

(60) Provisional application No. 63/025,463, filed on May 15, 2020.

(51) Int. Cl.

| | |
|---|---|
| ***A61K 38/28*** | (2006.01) |
| ***A61K 47/54*** | (2017.01) |
| ***A61K 47/65*** | (2017.01) |
| ***A61P 3/10*** | (2006.01) |
| ***C07K 14/62*** | (2006.01) |

(52) U.S. Cl.

CPC .............. *C07K 14/62* (2013.01); *A61K 38/28* (2013.01); *A61K 47/542* (2017.08); *A61K 47/65* (2017.08); *A61P 3/10* (2018.01)

(58) Field of Classification Search

CPC ...... C07K 14/62; A61K 38/28; A61K 47/542; A61K 47/65; A61P 3/10

See application file for complete search history.

(56) References Cited

U.S. PATENT DOCUMENTS

| | | | | |
|---|---|---|---|---|
| 5,922,675 | A | 7/1999 | Baker et al. | |
| 6,444,641 | B1 | 9/2002 | Flora | |
| 10,400,021 | B2 | 9/2019 | Liu et al. | |
| 11,965,039 | B2 * | 4/2024 | Shelton | C07K 14/472 |
| 2016/0368960 | A1 * | 12/2016 | Mezo | A61P 1/16 |

FOREIGN PATENT DOCUMENTS

WO WO 2019166411 * 9/2019

OTHER PUBLICATIONS

Nasrallah et al., Endocrinology and Diab. 5:31-37,(2012).*
International Search Report of the International Searching Authority pertaining to International Application No. PCT/US2021/032144; Date of Mailing: Oct. 22, 2021; 7 pages.
Written Opinion of the International Searching Authority pertaining to International Application No. PCT/US2021/032144; Date of Mailing: Oct. 22, 2021; 6 pages.

* cited by examiner

*Primary Examiner* — Gyan Chandra
(74) *Attorney, Agent, or Firm* — Perry Woo

(57) ABSTRACT

The presently described compounds relate to the treatment of Type I and/or Type II diabetes and/or hyperglycemia. More particularly, the described compounds relate to extended time action acylated insulin compounds that lower blood glucose, pharmaceutical compositions containing such compounds, therapeutic uses of such compounds, and an intermediate compound used to make the acylated insulin compounds.

13 Claims, No Drawings

Specification includes a Sequence Listing.

SEQUENCE LISTING

<160> NUMBER OF SEQ ID NOS: 8

<210> SEQ ID NO 1
<211> LENGTH: 21
<212> TYPE: PRT
<213> ORGANISM: Artificial Sequence
<220> FEATURE:
<223> OTHER INFORMATION: Synthetic Construct
<220> FEATURE:
<221> NAME/KEY: DISULFID
<222> LOCATION: (6)..(11)

<400> SEQUENCE: 1

Gly Ile Val Glu Gln Cys Cys Thr Ser Ile Cys Ser Leu Glu Gln Leu
1               5                   10                  15

Glu Asn Tyr Cys Asn
            20

<210> SEQ ID NO 2
<211> LENGTH: 29
<212> TYPE: PRT
<213> ORGANISM: Artificial Sequence
<220> FEATURE:
<223> OTHER INFORMATION: Synthetic Construct
<220> FEATURE:
<221> NAME/KEY: MOD_RES
<222> LOCATION: (29)..(29)
<223> OTHER INFORMATION: Epsilon amino group of Lys is chemically
      modified by conjugation with HO2C-(CH2)18-CO-gammaGlu-gammaGlu-
      gammaGlu-X-, wherein X is -Lys-Gly-, -Lys-(2-[2-(2-
      aminoethoxy)ethoxy]acetic acid)-, or -epsilonLys-Gly-

<400> SEQUENCE: 2

Phe Val Asn Gln His Leu Cys Gly Ser His Leu Val Glu Ala Leu His
1               5                   10                  15

Leu Val Cys Gly Glu Arg Gly Phe His Tyr Thr Pro Lys
            20                  25

<210> SEQ ID NO 3
<211> LENGTH: 29
<212> TYPE: PRT
<213> ORGANISM: Artificial Sequence
<220> FEATURE:
<223> OTHER INFORMATION: Synthetic Construct
<220> FEATURE:
<221> NAME/KEY: MOD_RES
<222> LOCATION: (29)..(29)
<223> OTHER INFORMATION: Epsilon amino group of Lys is chemically
      modified by conjugation with HO2C-(CH2)18-CO-gammaGlu-gammaGlu-
      gammaGlu-Lys-Gly-

<400> SEQUENCE: 3

Phe Val Asn Gln His Leu Cys Gly Ser His Leu Val Glu Ala Leu His
1               5                   10                  15

Leu Val Cys Gly Glu Arg Gly Phe His Tyr Thr Pro Lys
            20                  25

<210> SEQ ID NO 4
<211> LENGTH: 29
<212> TYPE: PRT
<213> ORGANISM: Artificial Sequence
<220> FEATURE:
<223> OTHER INFORMATION: Synthetic Construct
<220> FEATURE:
<221> NAME/KEY: MOD_RES
<222> LOCATION: (29)..(29)
<223> OTHER INFORMATION: Epsilon amino group of Lys is chemically
      modified by conjugation with HO2C-(CH2)18-CO-gammaGlu-gammaGlu-
      gammaGlu-Lys-(2-[2-(2-aminoethoxy)ethoxy]acetic acid)-

<400> SEQUENCE: 4

Phe Val Asn Gln His Leu Cys Gly Ser His Leu Val Glu Ala Leu His
1 5 10 15

Leu Val Cys Gly Glu Arg Gly Phe His Tyr Thr Pro Lys
20 25

<210> SEQ ID NO 5
<211> LENGTH: 29
<212> TYPE: PRT
<213> ORGANISM: Artificial Sequence
<220> FEATURE:
<223> OTHER INFORMATION: Synthetic Construct
<220> FEATURE:
<221> NAME/KEY: MOD_RES
<222> LOCATION: (29)..(29)
<223> OTHER INFORMATION: Epsilon amino group of Lys is chemically modified by conjugation with HO2C-(CH2)18-CO-gammaGlu-gammaGlu-gammaGlu-epsilonLys-Gly-

<400> SEQUENCE: 5

Phe Val Asn Gln His Leu Cys Gly Ser His Leu Val Glu Ala Leu His
1 5 10 15

Leu Val Cys Gly Glu Arg Gly Phe His Tyr Thr Pro Lys
20 25

<210> SEQ ID NO 6
<211> LENGTH: 9
<212> TYPE: PRT
<213> ORGANISM: Artificial Sequence
<220> FEATURE:
<223> OTHER INFORMATION: Synthetic Construct

<400> SEQUENCE: 6

Thr Glu Thr Ser Gln Val Ala Pro Ala
1 5

<210> SEQ ID NO 7
<211> LENGTH: 118
<212> TYPE: PRT
<213> ORGANISM: Artificial Sequence
<220> FEATURE:
<223> OTHER INFORMATION: Synthetic Construct
<220> FEATURE:
<221> NAME/KEY: DISULFID
<222> LOCATION: (41)..(104)
<220> FEATURE:
<221> NAME/KEY: DISULFID
<222> LOCATION: (53)..(117)
<220> FEATURE:
<221> NAME/KEY: DISULFID
<222> LOCATION: (103)..(108)

<400> SEQUENCE: 7

Met His His His His His His Gln Ala Ile Phe Val Leu Gln Gly Ser
1 5 10 15

Leu Asp Gln Asp Pro Glu Phe Glu Asn Leu Tyr Phe Gln Ile Glu Gly
20 25 30

Gly Arg Phe Val Asn Gln His Leu Cys Gly Ser His Leu Val Glu Ala
35 40 45

Leu His Leu Val Cys Gly Glu Arg Gly Phe His Tyr Thr Pro Lys Arg
50 55 60

Arg Glu Ala Glu Asp Leu Gln Val Gly Gln Val Glu Leu Gly Gly Gly
65 70 75 80

Pro Gly Ala Gly Ser Leu Gln Pro Leu Ala Leu Glu Gly Ser Leu Gln

-continued

```
                85                  90                  95

Arg Gly Ile Val Glu Gln Cys Cys Thr Ser Ile Cys Ser Leu Glu Gln
            100                 105                 110

Leu Glu Asn Tyr Cys Asn
        115


<210> SEQ ID NO 8
<211> LENGTH: 29
<212> TYPE: PRT
<213> ORGANISM: Artificial Sequence
<220> FEATURE:
<223> OTHER INFORMATION: Synthetic Construct

<400> SEQUENCE: 8

Phe Val Asn Gln His Leu Cys Gly Ser His Leu Val Glu Ala Leu His
1               5                   10                  15

Leu Val Cys Gly Glu Arg Gly Phe His Tyr Thr Pro Lys
            20                  25
```

EXTENDED TIME ACTION ACYLATED INSULIN COMPOUNDS

The present invention is in the field of treatment of diabetes and/or hyperglycemia. In particular, the present invention relates to compounds that lower blood glucose, pharmaceutical compositions containing such compounds and therapeutic uses of such compounds.

Insulin replacement therapy for diabetic patients would ideally parallel, as closely as possible, the pattern of endogenous insulin secretion in healthy individuals. The physiological demand for insulin may be separated into two phases: (a) a nutrient absorptive phase requiring a pulse of insulin to dispose of the meal-related blood glucose surge, also known as "prandial" insulin, and (b) a post-absorptive phase requiring a sustained delivery of insulin to regulate hepatic glucose output for maintaining optimal fasting blood glucose, also known as a "basal" insulin.

The need exists for alternative treatments for diabetes and/or hyperglycemia in patients. Some acylated insulin compounds are known, see, for example, U.S. Pat. Nos. 7,615,532, 10,400,021, 9,045,560, 9,018,161 but there remains a need for additional alternative treatments.

The present invention provides extended time action acylated insulin compounds that are useful in treating diabetes, reducing hemoglobin A1c, and/or reducing blood glucose levels in patients in need thereof. Compounds of the present invention have any of the following desirable characteristics: a slower clearance rate than known acylated insulins (e.g. insulin degludec), enhanced bioavailability, a more stable pharmacokinetic profile in humans over time, and/or an increased duration of action of the compound in vivo. In addition, compounds of the present invention exhibit a low chemical degradation rate, which indicates that they have increased chemical stability, and/or could achieve a shelf-life longer than known acylated insulins.

The invention provides a compound of Formula I:

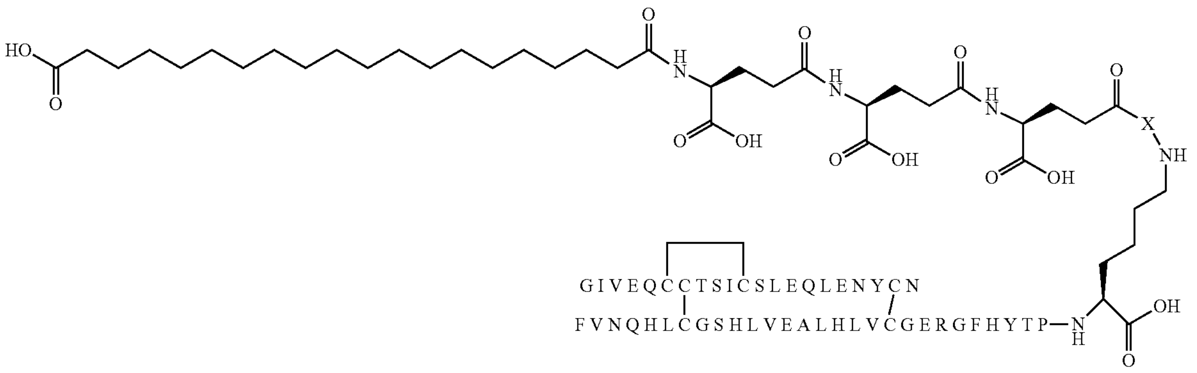

Effective insulin therapy for people with diabetes generally may involve the combined use of two types of exogenous insulin formulations: a rapid-acting, mealtime prandial insulin, and a longer-acting basal insulin which is administered once or twice daily to control blood glucose levels between meals. One or more characteristics of endogenous insulin that may be desirable to emulate include a binding affinity for the human insulin receptors, preferential binding to the human insulin receptors over the human IGF-1 receptor, phosphorylation of the human insulin receptors, and glucose lowering in the blood.

A desirable exogenous basal insulin should also provide an extended time action—that is, it would control blood glucose levels for preferably 24 hours or more, and most preferably for 168 hours or longer, without significant risk of hypoglycemia. Some basal insulins have a duration of action of 24 hours or more. A compound with an extended time-action profile, without significant variations in effectiveness during that time, may lower the risk of nocturnal hypoglycemia and allow greater variability in daily dosing times without increasing a patient's risk of hypoglycemia. Weekly administration is, therefore, highly desirable. Characteristics of an exogenous basal insulin that may be desirable include attenuated receptor binding, which can result in a reduced clearance rate from the bloodstream, and/or chemical stability at multiple concentrations, which could contribute to extended shelf-life stability and/or stability in a concentrated formulation, which would allow for the use in multi-dose devices.

wherein X is selected from the group consisting of -Lys-Gly-, -Lys-(2-[2-(2-aminoethoxy)ethoxy]acetic acid)-, and -εLys-Gly-; or a pharmaceutically acceptable salt thereof.

The compound of Formula I is therefore a modified human insulin consisting of: an A chain SEQ ID NO:1, wherein the native tyrosine amino acid residue at position A14 is mutated to a glutamic amino acid residue, and a B chain sequence of SEQ ID NO:2, wherein the native tyrosine amino acid residue at position B16 is mutated to a histidine amino acid residue, the native phenylalanine amino acid residue at position B25 is mutated to a histidine amino acid residue, and the native threonine amino acid residue at position B30 is deleted; wherein: a disulfide bond exists between the cysteine at position 6 of SEQ ID NO:1 and the cysteine at position 11 of SEQ ID NO:1, a disulfide bond exists between the cysteine at position 7 of SEQ ID NO:1 and the cysteine at position 7 of SEQ ID NO:2, and a disulfide bond exists between the cysteine at position 20 of SEQ ID NO:1 and the cysteine at position 19 of SEQ ID NO:2; and wherein the lysine amino acid residue at position B29 is chemically modified by conjugation of the epsilon-amino group of the lysine side-chain with $HO_2C$—$(CH_2)_{18}$—CO-γGlu-γGlu-γGlu-Lys-Gly-, $HO_2C$—$(CH_2)_{18}$—CO-γGlu-γGlu-γGlu-Lys-(2-[2-(2-aminoethoxy) ethoxy]acetic acid)-, or $HO_2C$—$(CH_2)_{18}$—CO-γGlu-γGlu-γGlu-εLys-Gly-; or a pharmaceutically acceptable salt thereof.

According to a preferred embodiment of the present invention, X is -Lys-Gly-; or a pharmaceutically acceptable salt thereof.

According to another preferred embodiment of the present invention, X is -Lys-(2-[2-(2-aminoethoxy)ethoxy]acetic acid)-; or a pharmaceutically acceptable salt thereof.

According to a further preferred embodiment of the present invention, X is -εLys-Gly-; or a pharmaceutically acceptable salt thereof.

A more preferred embodiment of the present invention, X is -Lys-Gly-; or a pharmaceutically acceptable salt thereof.

A preferred embodiment of the present invention provides a compound that is:

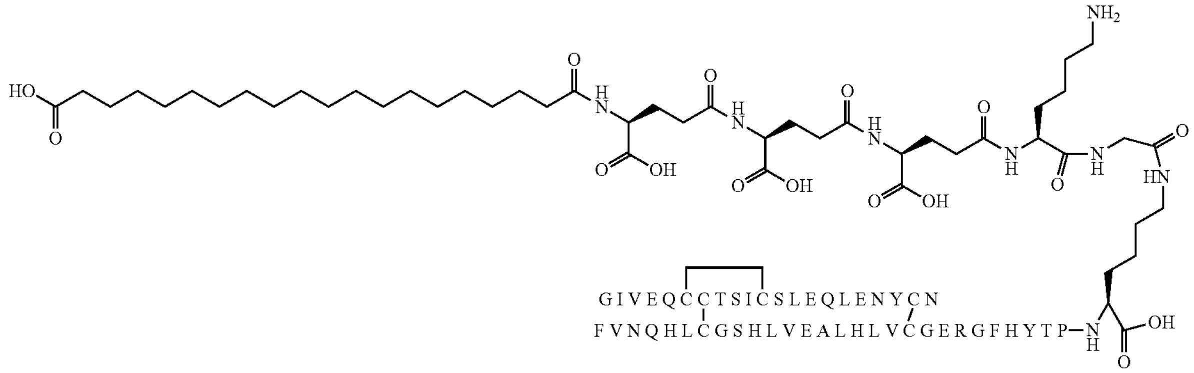

which is a compound of Formula I, consisting of an A chain of SEQ ID NO:1, a B chain of SEQ ID NO:3, wherein the epsilon-amino group of the lysine side-chain at position 29 on the B chain is chemically modified by conjugating with $HO_2C—(CH_2)_{18}—CO$-γGlu-γGlu-γGlu-Lys-Gly-; or a pharmaceutically acceptable salt thereof.

Preferably, the present invention provides a compound that is:

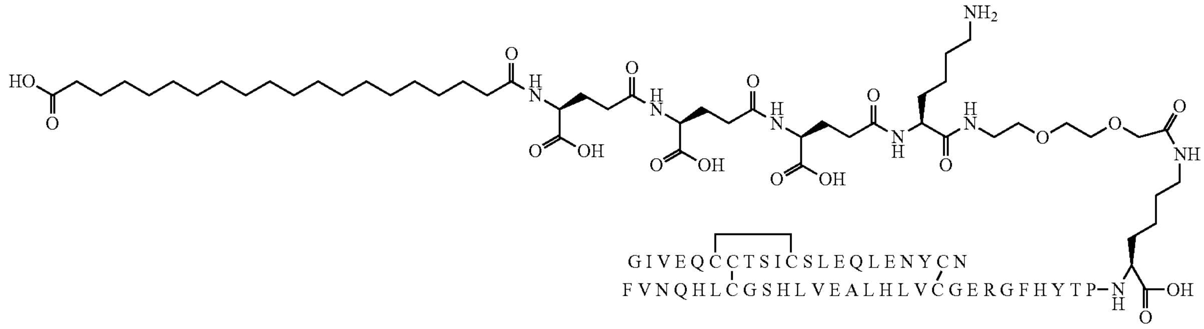

which is a compound of Formula I, consisting of an A chain of SEQ ID NO:1, a B chain of SEQ ID NO:4, wherein the epsilon-amino group of the lysine side-chain at position 29 on the B chain is chemically modified by conjugating with $HO_2C—(CH_2)_{18}—CO$-γGlu-γGlu-γGlu-Lys-(2-[2-(2-aminoethoxy)ethoxy]acetic acid)-; or a pharmaceutically acceptable salt thereof.

Preferably, the present invention includes a compound that is:

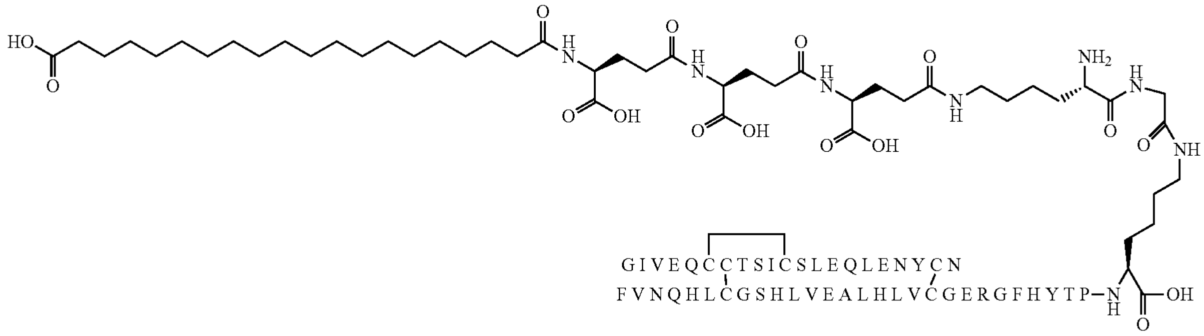

which is a compound of Formula I, consisting of an A chain of SEQ ID NO:1, a B chain of SEQ ID NO:5, wherein the epsilon-amino group of the lysine side-chain at position 29 on the B chain is chemically modified by conjugating with $HO_2C—(CH_2)_{18}—CO$-γGlu-γGlu-γGlu-εLys-Gly-; or a pharmaceutically acceptable salt thereof.

According to another aspect of the present application, there is provided a pharmaceutical composition comprising the compound of Formula I, or a pharmaceutically acceptable salt thereof and one or more pharmaceutically acceptable excipients.

Another aspect of the present application provides a method of treating Type I and/or Type II diabetes in a patient comprising administering to a patient in need thereof an effective amount of the compound of Formula I according to the present invention; or a pharmaceutically acceptable salt thereof, or a pharmaceutical composition comprising the compound of Formula I.

A further aspect of the present application provides a method of treating hyperglycemia in a patient comprising administering to a patient in need thereof an effective amount of the compound of Formula I according to the present invention; or a pharmaceutically acceptable salt thereof, or a pharmaceutical composition comprising the compound of Formula I.

Another aspect of the present application also provides a compound of Formula I, or a pharmaceutically acceptable salt thereof, for use in therapy.

The present application further provides a compound of Formula I, or a pharmaceutically acceptable salt thereof, for use in the treatment of diabetes and/or the treatment of hyperglycemia.

The compounds of the present invention are made using novel intermediate compounds, described below.

According to a further aspect of the present application, there is provided Compound A having the formula:

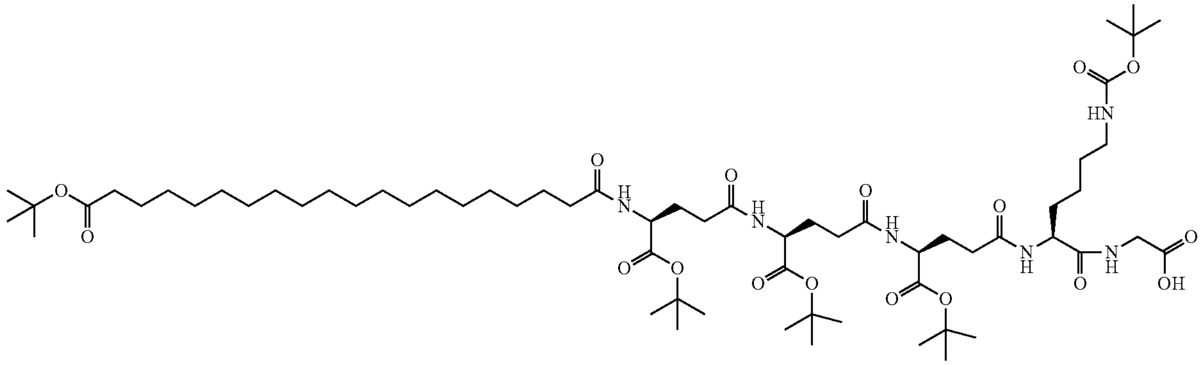 [SMILES: CC(C)(C)OC(=O)CCCCCCCCCCCCCCCCCCC(=O)N[C@@H](CCC(=O)N[C@@H](CCC(=O)N[C@@H](CCC(=O)N[C@@H](CCCCNC(=O)OC(C)(C)C)C(=O)NCC(=O)O)C(=O)OC(C)(C)C)C(=O)OC(C)(C)C)C(=O)OC(C)(C)C]

The present application also provides Compound B, having the formula:

disease or disorder or condition that would benefit from lowering glucose levels in the blood.

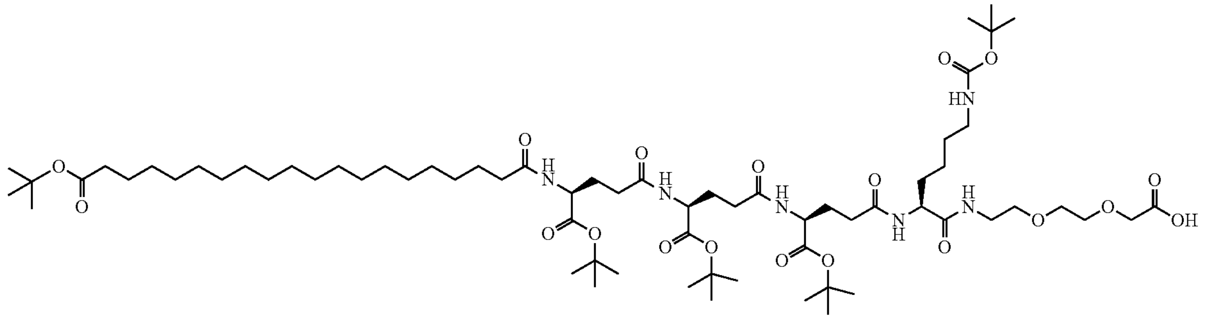 [SMILES: CC(C)(C)OC(=O)CCCCCCCCCCCCCCCCCCC(=O)N[C@@H](CCC(=O)N[C@@H](CCC(=O)N[C@@H](CCC(=O)N[C@@H](CCCCNC(=O)OC(C)(C)C)C(=O)NCCOCCOCC(=O)O)C(=O)OC(C)(C)C)C(=O)OC(C)(C)C)C(=O)OC(C)(C)C]

The present application also provides Compound C, having the formula:

Pharmaceutical compositions comprising a compound of the present invention may be administered parenterally to

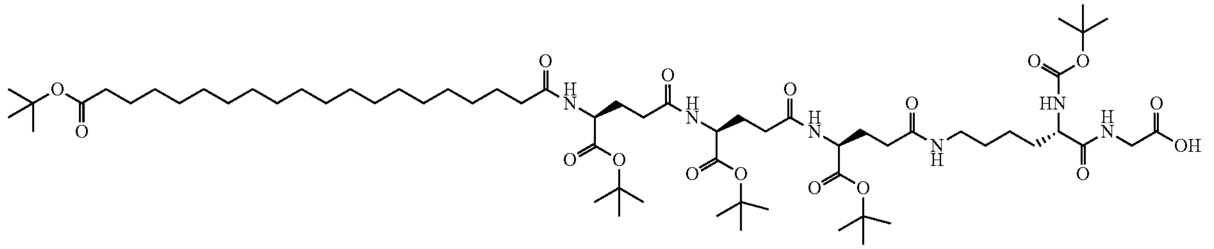 [SMILES: CC(C)(C)OC(=O)CCCCCCCCCCCCCCCCCCC(=O)N[C@@H](CCC(=O)N[C@@H](CCC(=O)N[C@@H](CCC(=O)NCCCC[C@H](NC(=O)OC(C)(C)C)C(=O)NCC(=O)O)C(=O)OC(C)(C)C)C(=O)OC(C)(C)C)C(=O)OC(C)(C)C]

Another aspect of the present invention provides a process for preparing a compound of Formula I using a compound selected from any one of Compounds A, B, and C.

Another aspect of the present application provides the use of any one of Compounds of Formula I, or a pharmaceutically acceptable salt thereof, in the manufacture of a medicament for the treatment of Type I and/or Type II diabetes and/or hyperglycemia.

The present application further provides the use of any one of Compounds A, B, or C in the preparation or manufacture of compounds of Formula I, or a pharmaceutically acceptable salt thereof.

The term "treatment" or "treating" as used herein refers to the management and care of a patient having diabetes or hyperglycemia, or other condition for which insulin administration is indicated for the purpose of combating or alleviating symptoms and complications of those conditions. The patient to be treated is an animal, and is, preferably, a human being.

As used herein, the term "effective amount" refers to the amount or dose of a compound of the present invention or a pharmaceutical composition containing a compound of the present invention, which upon single or multiple dose administration to the patient or subject, will elicit the biological or medical response of or desired therapeutic effect on a tissue, system, animal, mammal or human that is being sought by the researcher, veterinarian, medical doctor or other clinician. A dose can include a higher initial loading dose, followed by a lower dose.

The terms "patient," "subject," and "individual," are used interchangeably herein and refer to an animal. Preferably, the terms refer to humans. In certain embodiments, the patient, preferably a human, is further characterized with a patients in need of such treatment. Parenteral administration may be performed by subcutaneous, intramuscular or intravenous injection by means of a syringe, optionally a pen-like syringe, or mechanical driven injector. Alternatively, parenteral administration can be performed by means of an infusion pump.

Embodiments of the present invention provide pharmaceutical compositions suitable for administration, preferably weekly administration, to a patient comprising administering to a patient in need thereof a therapeutically effective amount of a compound of the present invention and one or more pharmaceutically acceptable excipients. Such pharmaceutical compositions may be prepared by any of a variety of techniques using conventional excipients for pharmaceutical products that are well known in the art. (Remington's Pharmaceutical Sciences, 21st Edition, University of the Sciences in Philadelphia, Philadelphia, PA, USA (2006)).

The claimed compounds may be used in simultaneous, separate or sequential combination with one or more additional therapeutic agents useful for treating diabetes and/or conditions related to diabetes. Non-limiting examples of the additional therapeutic agents that can be combined with the claimed compounds include: insulin or insulin analogs; biguanides; sulfonylureas; thiazolidinediones; dipeptidyl peptidase-4 ("DPP-4") inhibitors; sodium-dependent glucose transporter (SGLT2) inhibitors; incretin compounds such as glucagon-like-peptide-1 (GLP-1) or GLP-1 analogs, gastric inhibitory polypeptide (GIP) or GIP analogs, oxyntomodulin or oxyntomodulin analogs; or combinations of any of the foregoing agents. The claimed compounds and the additional therapeutic agent(s) can be administered either together through the same delivery route and device such as a single pill, capsule, tablet, or injectable formulation; or separately administered either at the same time in separate delivery devices or routes; or administered sequentially.

As used herein, "BHI" means biosynthetic human insulin, "TFA" means trifluoroacetic acid, "Boc" means tert-butyloxycarbonyl, "tBu" means tert-butyl, "PyBop" means benzotriazol-1-yl-oxytripyrrolidinophosphonium hexafluorophosphate, "DMF" means dimethylformamide, "DIEA" means diisopropylethylamine, "DCM" means dichloromethane, "HFIP" means hexafluoro isopropanol, "ACN" means acetonitrile, "Fmoc" means Fluorenylmethyloxycarbonyl, "DMSO" means dimethyl sulfoxide, "TCI" means two chain insulin, "SCI" means single chain insulin, "TIS" means triisopropylsilane, "TSTU" means (O—(N-Succinimidyl)-N,N,N',N'-tetramethyluronium tetrafluoroborate, "Su" means succinimidyl, "CpB" means Carboxypeptidase-B, "RP-HPLC" means reverse phase HPLC, "hr" means hour, "min" means minute, "EDTA" means ethylenediaminetetraacetic acid, "BSA" means bovine serum albumin, "HSA" means human serum albumin, "C20-OH" means icosanedioic acid, "γGlu" means L-glutamic acid connected through its side-chain gamma carboxyl group, "Lys" means L-lysine, "εLys" means L-lysine connected through its side-chain epsilon-amino group, and Gly means glycine.

Formula I contains the standard single letter amino acid codes for the amino acid residues of the insulin A chain and B chain, with the exception of residue 29 of the B chain, which is lysine, where the structure of that amino acid residue has been expanded. C20-OtBu is CO—$(CH_2)_{18}$—$CO_2$-tButyl or also referred to as 20-tert-butoxy-20-oxo-eicosanoic acid, γGlu(OtBu) is L-glutamic acid α-t-butyl ester, Lys(Boc) is L-lysine epsilon-amino t-butoxycarbonyl. A14E, B16H, B25H, desB30-human two chain insulin (TCI; A14E, B16H, B25H, desB30-BHI) refers to a modified human insulin wherein the tyrosine amino acid residue at position 14 on the A chain is mutated to a glutamic amino acid residue, the native tyrosine amino acid residue at position 16 on the B chain is mutated to a histidine amino acid residue, the native phenylalanine amino acid residue at position 25 on the B chain is mutated to a histidine amino acid residue, and the native threonine amino acid residue at position B30 is deleted.

Structures of 2-[2-(2-aminoethoxy)ethoxy]acetic acid, γGlu, and εLys.

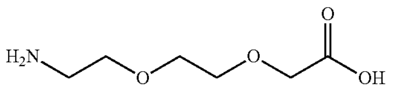

2-[2-(2-aminoethoxy)ethoxy]acetic acid

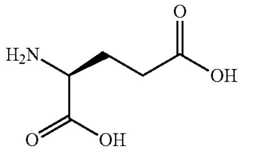

γ-Glu

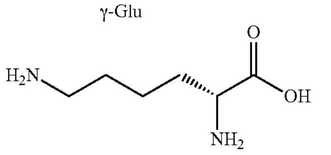

ε-Lys

Example 1 is a Compound of Formula I which may be generated by selective acylation of the epsilon-amino group of the lysine at position 29 of the B chain with the linker-fatty acid intermediate: C20-OtBu-γGlu(OtBu)-γGlu(OtBu)-γGlu(OtBu)-Lys(Boc)-Gly-OH, where C20-OtBu is 20-tert-butoxy-20-oxo-eicosanoic acid, γGlu(OtBu) is L-glutamic acid α-t-butyl ester connected through its side-chain gamma carboxyl group, Lys(Boc) is L-lysine epsilon-amino t-butoxycarbonyl, and Gly is glycine.

Example 2 is a Compound of Formula I which may be generated by selective acylation of the epsilon-amino group of the lysine at position 29 of the B chain with the linker-fatty acid intermediate: C20-OtBu-γGlu(OtBu)-γGlu(OtBu)-γGlu(OtBu)-Lys(Boc)-(2-[2-(2-aminoethoxy)ethoxy]acetic acid)-OH, where C20-OtBu is 20-tert-butoxy-20-oxo-eicosanoic acid, γGlu(OtBu) is L-glutamic acid α-t-butyl ester connected through its side-chain gamma carboxyl group, Lys(Boc) is L-lysine epsilon-amino t-butoxycarbonyl.

Example 3 is a Compound of Formula I which may be generated by selective acylation of the epsilon-amino group of the lysine at position 29 of the B chain with the linker-fatty acid intermediate: C20-OtBu-γGlu(OtBu)-γGlu(OtBu)-γGlu(OtBu)-εLys(Boc)-Gly-OH, where C20-OtBu is 20-tert-butoxy-20-oxo-eicosanoic acid, γGlu(OtBu) is L-glutamic acid α-t-butyl ester connected through its side-chain gamma carboxyl group, εLys(Boc) is L-lysine alpha amino t-butoxycarbonyl connected through its side-chain epsilon-amino group, and Gly is glycine, followed by removal of the acid labile Boc and tBu protecting groups.

Generation of a Compound of Formula I may occur in three main stages: 1) generation of A14E, B16H, B25H, desB30-BHI, 2) synthesis of the linker-fatty acid intermediate, and 3) acylation, deprotection, purification and salt exchange to isolate a Compound of Formula I.

The insulin portion of the present compounds may be prepared by a variety of techniques known to a person skilled in the art, such as via production of a precursor protein molecule using recombinant DNA techniques. The DNA, including cDNA and synthetic DNA, may be double-stranded or single-stranded. The coding sequences that encode the precursor protein molecule as described herein may vary as a result of the redundancy or degeneracy of the genetic code. The DNA may be introduced into a host cell in order to produce the precursor protein of the present invention. An appropriate host cell is either transiently or stably transfected or transformed with an expression system for producing the precursor protein. The host cells may be bacterial cells such as K12 or B strains of *Escherichia coli*, fungal cells such as yeast cells, or mammalian cells such as Chinese hamster ovary ("CHO") cells.

The expression vectors are typically replicable in the host organisms either as episomes or as an integral part of the host chromosomal DNA. Commonly, expression vectors will contain selection markers, e.g., tetracycline, neomycin, and dihydrofolate reductase, to permit selection of those cells transformed with the desired DNA sequences.

The compounds of the present invention may be prepared by a variety of procedures known in the art, as well as those methods described below. The specific synthetic steps for each of the routes described may be combined in different ways to prepare the compounds described herein. Examples 2 and 3 are prepared in a similar manner to that of Example 1.

PREPARATION OF ACYLATED INSULIN OF FORMULA I

Example 1

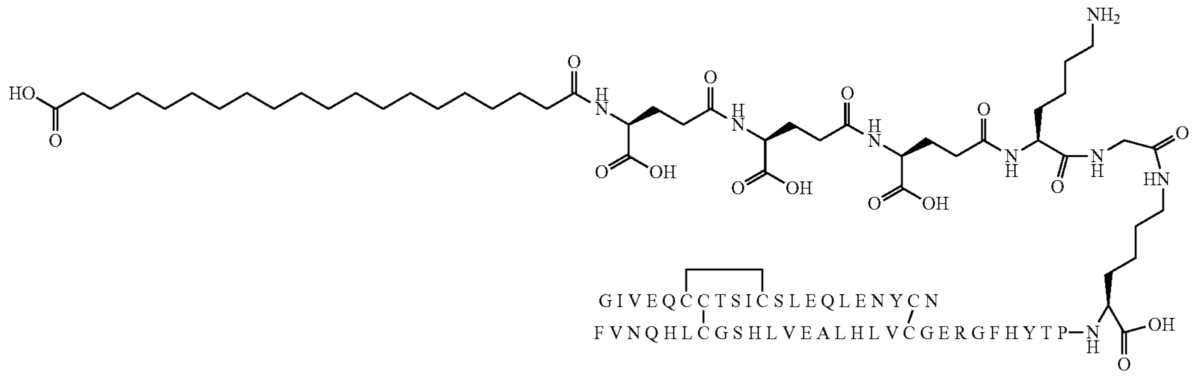

Example 1 is a compound of Formula I, consisting of an A chain of SEQ ID NO:1, a B chain of SEQ ID NO:3, wherein the Lys at position 29 on the B chain is chemically modified by conjugation with $HO_2C—(CH_2)_{18}—CO$-γGlu-γGlu-γGlu-Lys-Gly-.

Overview of the Synthesis of Example 1: Example 1 is generated by selective acylation of the epsilon-amino group of the lysine at position 29 of the B chain of the mature biosynthetic A14E, B16H, B25H, desB30-human two chain insulin (TCI; A14E, B16H, B25H, desB30-BHI) or by direct acylation of the analogous epsilon-amino group of the lysine at position 29 of the B chain of a single chain insulin (SCI; pre-proinsulin A14E, B16H, B25H, desB30-BHI) construct with the linker-fatty acid intermediate designated by Compound A (C20-OtBu-γGlu(OtBu)-γGlu-(OtBu)-γGlu(OtBu)-Lys(Boc)-Gly-OH). The preferred method is the acylation of the pre-proinsulin SCI construct. This method affords higher acylation efficiency of the epsilon-amino group of the lysine at position 29 of the B chain since the A1 and B1 amino terminus of the insulin molecule are blocked by the C-peptide and the leader sequence respectively. The fully mature two chain product of Example 1 is achieved through enzymatic digestion with CpB and Trypsin, subsequent to acylation and TFA deprotection steps. Even though acylation of the N-terminus of the SCI construct does occur, leading to a dual acylated side product, the enzymatic removal of the leader sequence also converts this material to the desired product.

Generation of the molecule occurs in three main stages:

1) *E. coli* expression and purification of the single chain pre-proinsulin construct (SCI): this could be used for the preferred acylation method, or it could be enzymatically processed into mature two chain insulin analog (TCI, A14E, B16H, B25H, desB30-BHI);

2) synthesis of the linker fatty acid intermediate (Compound A); and 3a) acylation, deprotection of TCI, or 3b) acylation, deprotection, and enzymatic digestion of SCI with subsequent purification and salt exchange to yield Example 1.

A new expression vector is developed and used in *E. coli* fermentation to generate the SCI insulin construct; it is comprised of the following sequence (SEQ ID NO:7):

```
MHHHHHHQAI FVLQGSLDQD PEFENLYFQI
1        10         20         30

EGGRFVNQHL CGSHLVEALH LVCGERGFHY
        40         50         60

TPKRREAEDL QVGQVELGGG PGAGSLQPLA
        70         80         90

LEGSLQRGIV EQCCTSICSL EQLENYCN
       100        110       118
```

Wherein, residues 1-34 constitute the leader peptide, residues 35-63 constitute the B-Chain (desB30T), residues 64-97 constitute a modified C-Peptide (des64K using native proinsulin numbering convention), and residues 98-118 constitute the A-Chain. The disulfide bonds correspond to the native insulin disulfide connectivity. The disulfide bonds are between C41 and C104; C53 and C117; and C103 and C108. Upon enzymatic digestion with CpB and Trypsin, the fully matured TCI analog is generated:

```
                                 (SEQ ID NO: 1)
GIVEQCCTSI CSLEQLENYC N
        10         20

                                 (SEQ ID NO: 8)
FVHQHLCGSH LVEALHLVCG ERGFHYTPK
        10         20        29
```

The disulfide bonds are between C7 (SEQ ID NO:1) and C7 (SEQ ID NO:8); C20 (SEQ ID NO:1) and C19 (SEQ ID NO:8); and C6 (SEQ ID NO:1) and C11 (SEQ ID NO:1). Note that both the SCI and TCI constructs are passed over standard RP-HPLC columns for purification and are lyophilized as solid TFA salts prior to acylation reactions. The linker fatty acid molecule is generated using solid-phase synthesis. This molecule may be generated using solution phase methods only, or in combination with solid-phase methods.

Conjugation of the linker fatty acid to TCI or SCI A14E, B16H, B25H, desB30-BHI is performed in dry organic solvent (DMSO) due to the solubility of the Boc/tBu protected amino acid-based linker fatty acid. Alternate protection/deprotection schemes could, however, be devised to render the linker fatty acid soluble in aqueous solution to minimize the use of organic solvents. Likewise, the acidic chemical transformation that removes the Boc/tBu protecting groups using trifluoroacetic acid (TFA) can be achieved by alternative means.

The Linker Fatty Acid Molecule, Compound a, is Generated Using Solid-Phase Synthesis Compound A (C20-OtBu)-γGlu(OtBu)-γGlu(OtBu)-γGlu(OtBu)-Lys(Boc)-Gly-OH, is generated by solid-phase peptide synthesis. Fmoc-Lys(Boc)-OH (769 mg, 1.6 mmol, 1.5 eq. relative to resin) is mixed with PyBop (849 mg, 1.6 mmol, 1.49 eq. relative to resin) and DIEA (1520 ul, 8.7 mmol, 8 eq.) in 10 mL DMF for 2 minutes and then transferred to a reaction vessel containing H-Gly-2-chlorotrityl-chloride resin (1.1 g, 0.99 mmol/g, 1.1 mmol; Peptides International RHG-1160-PI), which is pre-swelled in DCM and pre-washed with DMF. The slurry is mixed for 1.5 h, filtered and the resin is then washed well with DMF (Kaiser test is negative). The Fmoc protecting group is removed by treatment of the resin with 20% piperidine/DMF (10 mL, 30 min). After a DMF wash of the resin (40 mL), the Kaiser test is positive, the end product being H-Lys(Boc)-Gly-2-chlorotrityl-chloride resin (1.1 mmol in theory).

Fmoc-Glu-OtBu (701 mg, 1.6 mmol, 1.5 eq) is pre-activated (2 min) with PyBop (845 mg, 1.6 mmol, 1.49 eq.) using DIEA as base (1520 μl, 8.7 mmol, 8.0 eq) in 10 mL DMF, and transferred to the resin. The slurry is mixed for 3 hours, filtered, and the resin washed well with DMF (Kaiser test is negative). The Fmoc protecting group is removed by treatment of the resin with 20% piperidine/DMF (10 mL, 30 min) followed by a DMF wash of the resin (40 mL, Kaiser test is positive). The second and third Fmoc-Glu-OtBu residues are coupled to the resin by repeating the conditions above using a 1.5 hour coupling time.

After removing the last Fmoc protecting group, 20-tert-butoxy-20-oxo-icosanoic acid (660 mg, 1.60 mmol, 1.5 eq.) is pre-activated (2 min) with PyBop (845 mg, 1.6 mmol, 1.49 eq.) using DIEA as base (1520 μl, 8.7 mmol, 8.0 eq.) in 10 mL DMF, and transferred to the resin. The slurry is mixed for 3 hours, filtered, and the resin washed well with DMF (Kaiser test is negative). Cleavage from resin: the protected linker-fatty acid is cleaved from the resin by mixing with 30% HFIP/DCM (20 mL) for 1 hour. The resin is filtered off and rinsed well with DCM. The combined filtrates are evaporated to an oil in vacuo. The residual oil is diluted with ACN (15-20 mL) and evaporated in vacuo again to an oil. The sample is again dissolved with ACN (15-20 mL) and evaporated in vacuo to form an oil. A gentle stream of nitrogen evaporates the residual ACN to give 2.3 grams of crude, amorphous solid (theoretical yield=1.4 grams).

Purification: The crude sample is dissolved in 2 mL DMF and 20 mL ACN (including washes of flask). Water is added which gives 35 mL of a hazy solution. 10 mL additional ACN gives a clear solution (total volume equaled 45 mL (33% aqueous)). Purification is performed by loading the sample onto a semi-prep cyano RP-HPLC column (SilaChrom XDB1-CN; 10 μm, 100 Å; 2.1×25 cm). The sample is eluted using a 40-75% B gradient over 71 min, 15 mL/min, at 60° C. (A-Buffer=0.15% TFA in water and B-Buffer=ACN). Fractions determined to contain the desired product by analytical RP-HPLC are pooled, frozen and lyophilized to give 696 mg of Compound A as a white amorphous solid (52% of theory; 91% purity by RP-HPLC; obs. MW=1239.6 Dalton; theoretical. MW=1239.65 Dalton).

Compound B (C20-OtBu)-γGlu(OtBu)-γGlu(OtBu)-γGlu(OtBu)-Lys(Boc)-(2-[2-(2-aminoethoxy)ethoxy]acetic acid)-OH, is prepared substantially as described by the procedure for the synthesis of Compound A, but changing the starting resin to H-(2-[2-(2-aminoethoxy)ethoxy]acetic acid)-2-chlorotrityl-chloride resin (1.8 g, 0.62 mmol/g, 1.1 mmol; Peptides International RHX-11074-PI). Compound B is isolated by RP-HPLC as a white amorphous solid. Obs MW=1327.5 Dalton; theoretical. MW=1327.73 Dalton.

Compound C (C20-OtBu)-γGlu(OtBu)-γGlu(OtBu)-γGlu(OtBu)-εLys(Boc)-Gly-OH, is prepared substantially as described by the procedure for the synthesis of Compound A, but changing the Fmoc-Lys(Boc)-OH building block to Boc-L-Lys(Fmoc)-OH. Compound C is isolated by RP-HPLC as a white amorphous solid. Obs MW=1239.5 Dalton; theoretical. MW=1239.65 Dalton.

Acylation, Deprotection, Purification and Salt Exchange to Isolate Example 1

Acylation: Compound A ((C20-OtBu)-γGlu(OtBu)-γGlu(OtBu)-γGlu(OtBu)-Lys(Boc)-Gly-OH) (60.8 mg; 0.0437 mmol; 1.2 eq.; synthesis described above) and TSTU (12.04 mg 0.040 mmol; 1.1 eq.) are dissolved in 200 μL of dimethyl sulfoxide (DMSO). Diisopropylethylamine (DIEA, 25.3 μL; 0.145 mmol; 4 eq.) is added to this solution and the resulting mixture is incubated at room temperature for 30 minutes to generate the Compound A-OSu ester in DMSO and is used directly.

To a solution of the two chain insulin A14E, B16H, B25H, desB30-BHI (TFA salt; 205 mg; 0.0364 mmol) dissolved in 2 mL of dry dimethyl sulfoxide (DMSO), 1,8-Diazabicyclo[5.4.0]undec-7-ene (DBU; 81.6 μL 0.546 mmol, 15 eq., Sigma-Aldrich catalog 33482) is added and which is immediately followed by addition of the above Compound A-OSu ester in dry DMSO. The reaction mixture is stirred at ambient temperature for 12 minutes and added to a mixture of diethyl ether/DCM/TFA (30:10:0.2 v/v; 40 mL volume). The resulting white precipitate is isolated by centrifugation and triturated once with diethyl ether.

Deprotection (removal of Boc and OtBu groups): The above ether-wet white precipitate is treated with a mixture of TFA/triisopropylsilane (TIS)/water (92.5:5.0:2.5 v/v; 5 mL) for 20 minutes. Diethyl ether (40 mL) is added and the resulting precipitate is collected by centrifugation, washed once with ether, and dried. Reverse Phase (RP)-HPLC analysis shows the deprotection step to be complete (9% un-reacted A14E, B16H, B25H, desB30-BHI; 61% B29-acylated product; 13% A1, B29-bis-acylated product).

Purification: The above crude product is dissolved in 20 mM Tris HCl, pH 8/ACN (60:40 v/v; 15 mL). pH measurement using strips show an acidic pH between 2 and 3. The level is adjusted by the addition of 2 mL of 1 M Tris HCl (pH 8) to bring the solution also up to pH 8. Anion exchange chromatography with a GE Source 30Q anion exchange column (2.6×10 cm) using A-Buffer: 20 mM Tris HCl, pH 8/ACN (60/40 v/v). and B-Buffer: 20 mM Tris HCl, pH 8, with 0.5 NaCl/ACN (60/40 v/v) is performed as the initial purification step. The sample is loaded onto the column and washed with A-Buffer until a steady UV baseline is reached. The sample is eluted with a multi-step gradient: 0-8% B over 1 min, then 8-50% B over 59 min, and finally a 90% B hold for 12 min. The flow rate is set at 10 mL/minute, with UV monitoring at 225 nm and 280 nm and fraction collection time set for 0.5 minute. Analytical RP-HPLC with a Waters X Select CSH C18, 4.6×50 mm column is used to identify fractions containing the desired product. The desired fractions are pooled (~80 mL total volume) and diluted to 200 mL with milli-Q water.

Purification by RP-HPLC: The above diluted fractions are loaded onto a Kromasil C18 column (2.1×25 cm) and further purified using a standard TFA/Water/ACN gradient. Buffer- A=0.15% TFA/water and Buffer B=ACN. The sample is eluted with a multi-step gradient: 0-10% B over 1 min, then a 10-45% B over 71 min at a flow of 15 mL/min, the fraction collection time is set to 0.5 minute and a column temperature is 50° C. UV monitoring is performed at 225 nm and 280 nm. Analytical RP-HPLC with a Waters X Select CSH C18, 4.6×50 mm column is used to identify fractions containing the desired product. The desired fractions are pooled (~113 mL total volume; 99.8% by RP-HPLC).

Salt Exchange, Conversion to HCl salt: The elution buffers used for the salt HCl conversion are $A_1$-Buffer: 0.1 M aqueous Ammonium Chloride and $A_2$-Buffer: 0.01% HCl with Buffer B: ACN. The above pooled fractions are diluted with water to 200 mL and reloaded onto the Kromasil C18 column (2.1×25 cm) HPLC column. The column is washed with three column volumes of $A_1$-Buffer followed by three column volumes of $A_2$-Buffer. The sample is eluted using a gradient of 0-10% ($A_2$-B) over 1 min, then 10-70% ($A_2$-B) over 71 min with UV monitoring 225 nm and 280 nm. Fractions containing the desired product are identified by analytical RP-HPLC (column: Waters X Select CSH C18, 4.6×50 mm), pooled, frozen, and lyophilized to yield the compound of Example 1 as a white powder (153 mg, 0.023 mmol; 64% overall yield). Purity is confirmed by analytical RP-HPLC and found to be 98.9%. ESMS deconvoluted spectrum: obs. MW: 6531.2 Dalton; Theoretical MW: 6,533.4 Dalton.

Alternative method of Acylation of SCI: Compound A ((C20-OtBu)-γGlu(OtBu)-γGlu(OtBu)-γGlu(OtBu)-Lys (Boc)-Gly-OH) (584.6 mg; 0.424 mmol; 3.5 equiv) and TSTU (125.6 mg 0.417 mmol; 3.4 eq.) are dissolved in 1.0 mL of dry DMSO. DIEA (168.3 μL; 0.966 mmol; 8 eq.) is added and the resulting mixture is incubated at room temperature for 30 minutes to generate Compound A-O—(N-Succinimidyl ester (Compound A-OSu ester) in DMSO and is used directly.

To a solution of SCI-A14E, B16H, B25H, desB30-BHI (TFA salt; 1587 mg; 0.121 mmol) dissolved in 16 mL of dry DMSO, 1,8-Diazabicyclo[5.4.0]undec-7-ene (DBU; 452 μL 3.02 mmol, 25 eq., Sigma-Aldrich catalog 33482) is added, followed by addition of Compound A-OSu ester in DMSO in portions of (1.11 eq., 0.4 eq., 0.4 eq., 0.7 eq., 0.4 eq.) at approximately 10 min intervals for each portion. The progression of the reaction is monitored by analytical RP-HPLC. After the reaction mixture is stirred at ambient temperature for a total of 60 minutes, it is split into two equal 50 mL portions, filled with a mixture of diethyl ether/DCM/TFA (30:10:0.2 v/v; 40 mL volume). The resulting white precipitate is isolated by centrifugation and washed and triturated twice with 30 mL of diethyl ether.

Deprotection (removal of Boc and OtBu groups): The above ether-wet white precipitates are each treated with a mixture of TFA/triisopropylsilane (TIS; Aldrich)/water (92.5:5.0:2.5 v/v; 10 mL) for 30 minutes. To each mixture, diethyl ether (40 mL) is added and the resulting precipitates are collected by centrifugation and washed once with ether. The collected pellets are dried thoroughly to remove residual ether and crushed to a fine powder. RP-HPLC analysis shows the deprotection step to be complete (4% unreacted SCI-A14E, B16H, B25H, desB30-BHI; 51% B29-acylated product; 38% N-Terminus, B29 bis-acylated product).

Enzymatic Digestion (removal of leader sequence and C-peptide): The dry powdered crude product is completely dissolved in 0.1 M Tris HCl pH 8 (600 mL). To this solution, 6.0 mL of a 0.1 M $CaCl_2$ solution, 6.363 mL of Carboxypeptidase-B stock solution (2.9 mg/mL in water), and 1.587 mL of Trypsin stock solution (1.0 mg/mL in water) is added. The solution is incubated at room temperature for 120 min. Analytical RP-HPLC and LC-MS analysis confirms complete generation of mature compound of Example 1 (IFA-197). The solution is acidified with 45 mL of glacial acetic acid (pH 2-3 by pH paper).

Isolation of Digested Product by Preparative RP-HPLC: The desired product contained in the above acidified digest solution is isolated in a series of preparative RP-HPLC purification runs. Generally, the desired product is eluted from the RP-HPLC column using a linear water/ACN gradient containing 0.05% TFA, fractions containing the desired product are pooled, frozen, and lyophilized. If the desired purity is achieved during this step, Anion Exchange (AEX) chromatography can be omitted.

Initial Purification Step by Preparative AEX Chromatography (Optional): AEX with a GE Source 30Q anion exchange column (2.6×11.5 cm) using A-Buffer: 20 mM Tris HCl, pH 8/ACN (60/40 v/v). and B-Buffer: 20 mM Tris HCl, pH 8, with 0.5 NaCl/ACN (60/40 v/v) is performed to remove any remaining C-peptide or leader sequence. Two batches of lyophilized powder are dissolved with 12 mM Tris, pH 8/40% ACN (with additional 1 M Tris HCl, pH 8 buffer, to bring the pH up 8). Each solution is subsequently loaded onto the AEX column which is equilibrated with 100% A-Buffer and washed with A-buffer until a steady UV baseline is reached. The samples are eluted with a linear gradient of 0-50% B over 60 min and a 100% B hold for 12 min. The flow rate is set at 10 mL/minute, with UV monitoring at 225 nm and 280 nm and fraction collection time set for 0.5 minute.

Analytical RP-HPLC with a Waters XSelect CSH C18, 4.6×50 mm column is used to identify fractions containing the desired product. The desired fractions are pooled (225 mL total volume) and stored at 4° C. until the desalting/HCl conversion step.

Salt Exchange; Conversion to HCl salt: Desalting and conversion to HCl salt form is achieved simultaneously through preparative RP-HPLC using a Phenomenex Luna C18(2) column (2.1×25 cm, 5 μm, 100 Å), with $A_1$-Buffer: 0.1 M aqueous Ammonium Chloride and $A_2$-Buffer: 0.01% HCl with Buffer B: ACN. The pooled solution from the AEX purification step is split into three equal parts (75 mL each). Each part is diluted with 75 mL of milli-Q water and 1.5 mL glacial Acetic Acid. Each solution (~151 mL) is loaded onto the RP-HPLC column equilibrated with $A_1$-Buffer, washed with 2 column volumes of with $A_1$-Buffer, 2 column volumes of $A_2$-Buffer. The samples are eluted with linear gradient of 5-10% ($A_2$-B) over 1 min, then 10-40% ($A_2$-B) over 71 min at 15 mL/min, at 55° C.). Fractions containing the desired product are identified by RP-HPLC (column: Waters XSelect CSH C18, 4.6×50 mm), pooled, frozen, and lyophilized to yield Example 1-HCl salt as a white amorphous powder (354 mg, 0.054 mmol; 45% overall yield). Purity is confirmed by analytical RP-HPLC and found to be 99%. ESMS: deconvoluted spectrum: Observed MW: 6531.2 Dalton; Theoretical MW: 6,533.4 Dalton.

Example 2

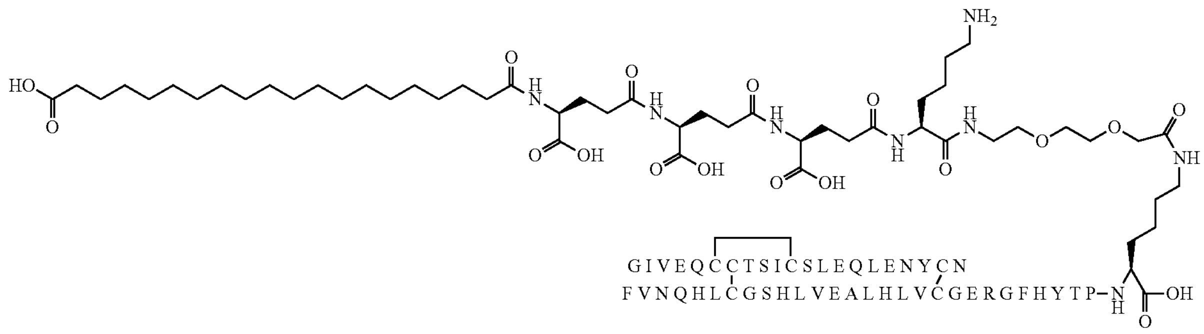

Example 2 is a compound of Formula I, consisting of an A chain of SEQ ID NO:1, a B chain of SEQ ID NO:4, wherein the epsilon-amino group of the Lys side-chain at position 29 on the B chain is chemically modified by conjugating with $HO_2C—(CH_2)_{18}—CO$-γGlu-γGlu-γGlu-Lys-(2-[2-(2-aminoethoxy)ethoxy]acetic acid)-.

Example 2 is prepared substantially as described by the procedures of Example 1, except ((C20-OtBu)-γGlu(OtBu)-γGlu(OtBu)-γGlu(OtBu)-Lys(Boc)-(2-[2-(2-aminoethoxy) ethoxy]acetic acid)-OH) (Compound B) is used in the acylation step. ESMS: deconvoluted spectrum: Observed MW: 6620.1 Dalton; Theoretical MW: 6,621.5 Dalton.

Example 3

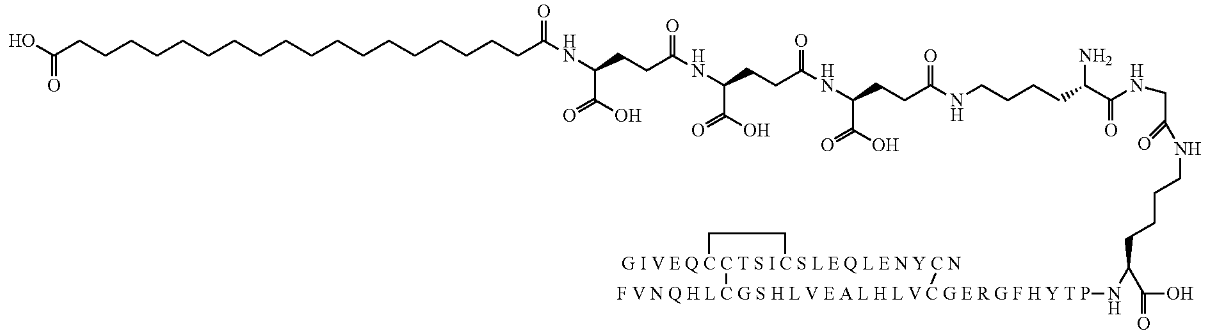

Example 3 is a compound of Formula I, consisting of an A chain of SEQ ID NO:1, a B chain of SEQ ID NO:5, wherein the epsilon-amino group of the Lys side-chain at position 29 on the B chain is chemically modified by conjugating with $HO_2C—(CH_2)_{18}—CO$-γGlu-γGlu-γGlu-εLys-Gly-.

Example 3 is prepared substantially as described by the procedures of Example 1, except ((C20-OtBu)-γGlu(OtBu)-γGlu(OtBu)-γGlu(OtBu)-εLys(Boc)-(Gly)-OH) (Compound C) is used in the acylation step. ESMS deconvoluted spectrum: obs. MW: 6532.0 Dalton; Theoretical MW: 6,533.4 Dalton.

In Vitro Receptor Affinity

Examples 1, 2, and 3 and control compounds (biosynthetic human insulin (BHI), and insulin-like growth factor 1 (IGF-1)) are tested in human insulin receptor (hIR) and human IGF-1 receptor (hIGF-1R) scintillation proximity assay (SPA) competitive radioligand binding assays using membranes prepared using differential centrifugation steps from stably-transfected 293 HEK cells over expressing the recombinant hIR-A, hIR-B or hIGF-1R.

Stably transfected cell lines are prepared by subcloning receptor cDNA using a pcDNA3.1 expression plasmid into human embryonic kidney (HEK) 293 cells followed by selection with Geneticin. Cell lines generated are human IR-A, human IR-B containing a C-terminal C9 tag (TETSQVAPA (SEQ ID NO:6)), human IGF-1R and rat IR-A containing a C-terminal C9 tag (TETSQVAPA). Cells are grown in a 5% $CO_2$, humidified environment. Typically, cell pellets from passages 6 to 12, depending on the receptor, are frozen for preparation of membranes.

Frozen cell pellets are thawed in ice-cold Homogenization/Resuspension Buffer (50 mM Tris-HCl, pH 7.5) containing one Complete® protease inhibitor tablet with EDTA (Roche Diagnostics) per 50 mL of buffer. The cells are homogenized with an overhead motor driven Teflon-glass Potter-Elvehjem homogenizer using 15 to 20 strokes, followed by centrifugation at 1100×g for 10 minutes at 4° C. The supernatant is saved on ice and the pellets ae homogenized as before and centrifuged at 1100×g for 10 minutes at 4° C. All supernatants are combined and subsequently centrifuged at 35,000×g for 60 minutes at 4° C. The pellet is resuspended in buffer (4 to 5 mL/g of starting cell paste) containing protease inhibitors and quick frozen in liquid nitrogen prior to storage at −80° C. Protein concentration are determined using a bicinchonic acid (BCA) kit (Thermo-Scientific) with BSA as standard.

Receptor binding affinities ($K_i$) are determined from a competitive radioligand binding assay with either human recombinant (3-[$^{125}$I]-iodotyrosyl-A14)-insulin (2200 Ci/mmol) or human recombinant [$^{125}$I]-insulin-like growth factor-1 (1853 Ci/mmol), both obtained from Perkin Elmer. The assays are performed with a scintillation proximity assay (SPA) method using polyvinyltoluene (PVT) wheat germ agglutinin-coupled SPA beads (Perkin Elmer). Assay Buffer (50 mM Tris-HCl, pH 7.5, 150 mM NaCl) contained either 0.1% (w/v) fatty-acid free BSA, 0.001% (w/v) NP-40 (4-Nonylphenyl-polyethylene glycol), or 0.1% (w/v) fatty-acid free HSA and is used for all compound testing and reagent preparation. Ten-point concentration response curves using three-fold serial dilutions of test samples or controls are prepared in assay buffer using a Freedom/Evo robot (Tecan®). Fifty µL of compound dilution is added to a 96-well white, clear-bottom microplate (Corning) with a TeMO robot (Tecan®) followed by radioligand (50 µL), membranes (50 µL) and SPA beads (50 µL), all added using a Multiflo F/X (Biotek) bulk dispensing instrument. The final concentration of radioligand is ~40 pM and the amount of SPA beads added is 0.15 mg/well.

The affinity constant (Ki) is calculated from the $IC_{50}$ value based upon the equation $Ki=IC_{50}/(1+L^*/Kd)$ where L* equals the concentration of radioligand used in the experiment and Kd equals the equilibrium binding affinity constant of the radioligand for the respective receptor, determined from saturation binding analysis.

Geometric mean, $Ki=10^{(\text{Arithmetic Mean of Log Ki Values})}$

Error is calculated using the Delta method, where SEM=GeoMean×((Standard Deviation of Log 10 *Ki* values)/(square root of *n*))×ln 10

Tables 1 Å, B, C: Human Insulin Receptor Subtypes A and B (hIR-A and hIR-B) and Human Insulin-like Growth Factor-1 Receptor (hIGF-1R) Binding Affinity, Ki values are geometric means and SEM is the error calculated using the Delta method.

TABLE 1A

| 0.1% (w/v) BSA | | | |
|---|---|---|---|
| | Ki, nM (SEM, n) Test Compound | | |
| | hIR-A | hIR-B | hIGF-1R |
| Example 1 | 413 (55, 3) | 253 (41, 3) | >19800 (NC, 1/3) |
| Example 2 | 423 (52, 3) | 190 (32, 3) | >19900 (NC, 1/3) |
| Example 3 | 404 (60, 3) | 303 (16, 3) | >19500 (NC, 1/3) |
| BHI | 0.260 (0.038, 6) | 0.167 (0.017, 6) | 124 (11, 3) |
| IGF-1 | 7.73 (0.75, 3) | 67.3 (9.9, 3) | 0.147 (0.023, 6) |

TABLE 1B

| 0.001% (w/v) NP-40 | | | |
|---|---|---|---|
| | Ki, nM (SEM, n) Test Compound | | |
| | hIR-A | hIR-B | hIGF-1R |
| Example 1 | 68.2 (20.5, 3) | 64.0 (7.9, 3) | >19200 (NC, 1/3) |
| Example 2 | 124 (2, 3) | 70.1 (4.9, 3) | >19300 (NC, 1/3) |
| Example 3 | 86 (15.8, 3) | 60.2 (10.8, 3) | >18900 (NC, 1/3) |
| BHI | 0.304 (0.073, 6) | 0.313 (0.038, 6) | 108 (38, 3) |
| IGF-1 | 10.3 (3.9, 3) | 86.1 (12.5, 3) | 0.187 (0.015, 6) |

TABLE 1C

| 0.1% (w/v) HSA | | | |
|---|---|---|---|
| | Ki, nM (SEM, n) Test Compound | | |
| | hIR-A | hIR-B | hIGF-1R |
| Example 1 | 274 (38, 3) | 177 (21, 3) | ND |
| Example 2 | 240 (38, 3) | 145 (9, 3) | ND |
| Example 3 | 334 (20, 3) | 220 (24, 3) | ND |
| BHI | 0.221 (0.042, 6) | 0.149 (0.016, 6) | ND |
| IGF-1 | 7.79 (0.12, 3) | 54.3 (6.6, 3) | ND |

The data in the Tables 1A, 1B, and 1C show that Examples 1, 2, and 3 bind to human IR-A and human IR-B with very low binding to hIGF-R using either 0.1% BSA, 0.001% NP-40, or 0.1% HSA in the assay buffer.

Receptor Functional Activation

The insulin receptor contains an intracellular tyrosine kinase domain that upon ligand binding auto-phosphorylates its own tyrosine residues to allow recruitment of adaptor proteins that act to induce the insulin signaling pathways. Functional cellular activity for stimulation of receptor auto-phosphorylation on tyrosine residues is determined after ligand treatment of HEK293 cells over-expressing hIR-A, hIR-B, or hIGF-1R, each with a C-terminal C9 epitope (TETSQVAPA, SEQ ID NO:6).

HEK293 cells over-expressing hIR-A or hIR-B-C9 are trypsinogenized and spun down at 1000 rpm. The cells are re-suspended with starvation medium containing DMEM high glucose without sodium pyruvate plus 0.1% BSA and seeded in 96 well poly-D-lysine coated plates at density of 50K-60K cells/well. The cells are incubated under standard tissue culture conditions overnight. To assess the effect of albumin binding, stimulation of cells is performed in a medium containing DMEM high glucose without sodium pyruvate plus 0.1% of BSA. After stimulation of hIR-A or hIR-B cells with various concentrations of ligand ranging from 10 to 0.0000169 µM at 37° C. for 60 minutes, the cells are lysed by lysis buffer containing 50 mM Tris (pH7.5), 150 mM NaCl, 1% NP40 and freshly added completed protease inhibit cocktail (Pierce A32955) plus 2 mM Vanadate (Sigma S6508) on the assay day. The level of tyrosine auto-phosphorylation by the kinase domain of each receptor is determined by applying the cell lysates to an ELISA plate; wherein, the activated receptor is captured by an antibody to either IR (Ab 83-14) at 3.5 µg/ml for IR-A or the C9 epitope tag at 2 µg/ml for IR-B, followed by detection of the level of tyrosine phosphorylation with the anti-phosphotyrosine horse radish peroxidase conjugate, HRP antibody (Millipore 16-105) at 1:5000 ratio.

For IR ELISA, 96-well plates are coated with either Ab 83-14 at 3.5 µg/mL for IR-A or 2 µg/mL anti-C9 Ab for IR-B. Antibodies are diluted in 20 mM Na Carbonate, pH 9.6 and incubated overnight at 4° C. On the second day, the plates are washed 3 times with TBST (1×TBS containing 0.1% Tween 20). The plates are blocked with 1% BSA in TBST for 1 hour. The blocking buffer is removed, and the cell lysate is applied to the plates. The plates are incubated at room temperature for 1 hour on a shaker. The plates are washed 3 times with 1×TBST. The secondary antibody (anti-phosphotyrosine-HRP (Millipore 16-105) at 2 µL in 10 mL (1/5000) in TBST containing 1× proteinease and phosphatase inhibitor cocktail) is applied. The plates are further incubated for 1 hour at room temperature on a shaker. To develop the signal for pIR, the plates are washed 4 times with TBST. The TMB substrate (Pierce 34021) is added to the plates in a volume of 100 μL/well and incubated at room temperature for 5 minutes. The reaction is stopped by adding 100 μL/well of 2N $H_2SO_4$ and the plated incubated for 5 minutes. The plates are read at OD450 nm.

Insulin Receptor Activation, 0.1% Casein (BSA-Free Method)

In order to measure the effect of the Examples on IRA and IRB phosphorylation in the presence of 0.1% casein, hIRA-HEK293-zeo or hIRB-C9-HEK293-G418 cells are first plated at 60,000 cells/well in a 96-well poly-D-lysine coated plate (Biocoat 354461) in DMEM with high glucose and no sodium pyruvate (Gibco 11965-084) with 0.1% BSA. The cells are next incubated overnight at 37° C. in a tissue culture incubator. 96-well ELISA plates are also coated with 3.5 μg/mL anti-insulin receptor antibody 83-14 (for the IRA assay) or 2.0 μg/mL anti-C9 antibody (for the IRB assay) in a 20 mM sodium carbonate buffer (pH 9.6) and incubated overnight at 4° C.

The next day, the ELISA plates are washed 3× with 200 μL of wash buffer (TBS-T with 0.1% Tween®) and blocked for at least an hour with 1% BSA in TBS-T. Assay media is prepared with 0.1% casein in DMEM with high glucose and no sodium pyruvate. The following compounds are diluted to the respective concentration in assay media: human Insulin to 200 nM, Examples to 60 hIGF-1 to 20 μM, and AspB10 to 200 nM. The compounds are serially diluted in a 1:3 dilution. The cell plates are rinsed twice with 50 μL assay media and then 50 μL of assay media and 50 μL of the diluted compounds are transferred to individual wells of the cell plates. 200 nM BHI is transferred. The plates are incubated for 1 hour at 37° C.

Protease inhibitors (Pierce A32965) and sodium orthovanadate (final concentration of 2 mM) are added to lysis buffer (50 mM Tris pH 7.4, 150 mM NaCl, and 1% NP40). After a 1 hour incubation, cell plates are first washed with 100 μL cold DPBS and lysed in 100 μL lysis buffer for 15 min at 4° C. The cell lysate plates are mixed and 300 μL of BHI treated cell lysate is transferred to the first column of a dilution plate from the cell plate half treated with BHI. 200 μL of lysis buffer is added to the other eleven columns of this dilution plate, and the lysate is serially diluted 1:3 eleven times by transferring 100 μL of the lysate to 200 μL of lysis buffer and repeating eleven times. 10 μL of lysate is transferred from the cell plate treated with compounds to a dilution plate, and 190 μL of lysis is added to each well. The ELISA plates are washed as described before and then 100 μL of the diluted lysate is transferred to the appropriate ELISA plates. The plates are incubated at room temperature on a shaker for one hour.

The plates are washed as before and 100 μL of secondary antibody diluted 1:5000 in TBST (with protease inhibitors and 40 μM sodium orthovanadate) is added to each plate. The plates are incubated at room temperature on a shaker for one hour. The plates are washed as before and 50 μL TMB is added to the plate to develop for about 2 minutes. The TMB reaction is stopped with 50 μL 2N sulphuric acid and the plates are read at 450 nm.

Functional potency is reported as the concentration eliciting a half-maximal response ($EC_{50}$) relative to a maximally efficacious concentration (100 nM) of the positive control, human insulin (hIR-A and hIR-B phosphorylation assays) or 10 nM of the positive control hIGF-1 (hIGF-1R phosphorylation assay). $EC_{50}$ values are determined from 4-parameter logistic non-linear regression analysis (NGR Screener 13). If necessary, curve top or bottom parameters are set to 100 or 0, respectively.

Reported values for $EC_{50}$ are shown as geometric mean and the standard error of the mean (SEM) is calculated using the Delta Method, with the number of independent determinations indicated by "n" (Table 2).

TABLE 2

Human Insulin Receptor Subtypes A and B (hIR-A and hIR-B) Activation geomean, (SEM, n)

| | 0.1% BSA EC50, nM (SEM, n) | | 0.1% Casein EC50, nM (SEM, n) | |
|---|---|---|---|---|
| | Test Compound | | | |
| | hIR-A | hIR-B | hIR-A | hIR-B |
| Example 1 | 2550<br>(147, 3) | 1560<br>(156, 3) | 588<br>(42.9, 3) | 145<br>(10.8, 3) |
| Example 2 | 3035<br>(229, 3) | 1791<br>(85, 3) | 478<br>(72.1, 3) | 124<br>(14.7, 3) |
| Example 3 | 3182<br>(240, 3) | 1219<br>(68, 3) | 627<br>(40.4, 3) | 183<br>(12.7, 3) |
| BHI | 3.36<br>(0.176, 3) | 2.37<br>(0.231, 3) | 5.19<br>(0.702, 3) | 1.89<br>(0.319, 3) |
| IGF-1 | 240<br>(25.4, 3) | 771<br>(14.7, 3) | 156<br>(10.2, 3) | 577<br>(60.1, 3) |

The data in Table 2 show that Examples 1, 2, and 3 bind and stimulate the human insulin receptor A and B.

Evaluation of In Vivo Potency in a Rat Model of Type 1 Diabetes

The glucose-lowering and pharmacokinetics of Examples 1, 2, and 3 are investigated in streptozotocin (STZ)-treated rat diabetes model. Male Sprague-Dawley rats, 400-425 gram body weight, are obtained from Envigo, Indianapolis, Indiana. After acclimation for approximately one week, the rats are anesthetized with isoflurane and given a single injection of Zanosar (89256, Teva Parenteral Medicines, 40 mg/kg, IV). The rats are used in studies 3 days after injection of Zanosar; only animals with non-fasted blood glucose between 400-550 mg/dl are used in these studies.

The rats are distributed into groups to provide comparable variance in blood glucose and body weight; rats are randomized. The blood glucose is measured using Accu-Chek Aviva glucometer (Roche).

Test articles (peptide solutions; 1 mL/kg; subcutaneous; single dose on day 1 of the dosing phase) or vehicle (10 mM Tris, 19 mg/mL glycerol, 3.15 mg/mL m-cresol, pH 7.6; 1 mL/kg; subcutaneous; single dose on day 1 of the dosing phase) are dosed based on animals body weight at 0800 on day 1 of dosing. Blood samples for glucose measurements are collected by tail bleed. The animals have free access to food and water throughout the experiment. Plasma samples from these studies are sent for analysis of compound levels.

At 0, 1, 2, 4, 6, 8, 10, 12, 18, 24, 36, 48, 60, 72, 84, 96, 108, and 120 hours post dose, whole blood is collected for whole blood glucose using a glucometer. Values are recorded in duplicate unless values differed by more than 30 mg/dL. If this occurs, a triplicate value is recorded. If a rat drops below 35 mg/dL glucose, the entire group is dosed orally with 2 mL of 50% dextrose except rats who are >100 mg/dL within the same group. Rescued rats are observed and blood glucose measured every 2 to 4 hours after dextrose load. During the observation period, if a rat falls below 35 mg/dL glucose, the entire group is orally dosed with 2 mL of 50% dextrose except rats who are >100 mg/dL within the same group. Observation continues with measurement of blood glucose every 2 to 4 hours after dextrose load. If a rat is dosed orally with 2 mL of 50% dextrose, all subsequent recorded glucose values are excluded from study calculations. Even if animals are rescued, they continue to be on study to collect PK time points as PK is not affected by a dextrose bolus.

Immunoaffinity-LC/MS Rat Plasma Assay: To characterize the PK of the Examples, plasma samples (10 μL aliquots) are analyzed for intact insulin concentrations via immunoprecipitation followed by LC/MS analysis. Standards and blank samples are prepared in 100% control rat plasma using an Example, and a stable isotope-labeled antibody (unrelated to an Example) is added to all standards and samples as an internal standard. For immunoprecipitation, a biotin-labeled anti-human murine antibody (Fitzgerald, 10R-I134E) is used as a capture reagent, which is subsequently bound by Dynal M-280 streptavidin-coated magnetic beads (Invitrogen 60210). The magnetic bead-immobilized samples are washed with 0.1% CHAPS followed by PBS, and an Example is eluted with a solution containing 20% ACN, 2% aqueous formic acid, and 20% Invitrosol (Invitrogen, 46-5553). Plasma samples are quantified using a Thermo Q/Exactive Plus mass spectrometer over the range of 0.01 to 5.3 μg/mL (1.6 to 802 nM).

The non-compartmental pharmacokinetic analysis is conducted using Phoenix WinNonLin v8.1. For the rat PK analysis, the concentrations used in the estimation of the elimination half-lives are averaged from 44 to 120 hours post-dose for the 50 nmol/kg dose group, from 32 to 120 hours post-dose for the 100 nmol/kg dose group, from 18 to 120 hours post-dose for the 200 nmol/kg dose group, and from 18 to 120 hours post-dose for the 400 nmol/kg dose group.

Tables 3A, 3B: The glucose-lowering (3 Å) and pharmacokinetics effects (3B) of Example 1 in streptozotocin (STZ)-treated rat diabetes model.

TABLE 3A

Glucose-lowering of Example 1 in Male, STZ-treated, Sprague-Dawley Rats Following Single Subcutaneous Administrations of 50, 100, 200, or 400 nmol/kg of Example 1.

| | Avg Glucose mg/dl (SEM) n = 5 | | | | |
|---|---|---|---|---|---|
| Time (Hours) | Vehicle | Example 1 (50 nmol/kg) | Example 1 (100 nmol/kg) | Example 1 (200 nmol/kg) | Example 1 (400 nmol/kg) |
| 0 | 559 (15.3) | 509 (9.08) | 535 (17.3) | 524 (10.4) | 496 (13.4) |
| 1 | 510 (21.7) | 454 (18.8) | 492 (13.8) | 364 (64.4) | 196 (35.6) |
| 2 | 504 (14.3) | 327 (43.0) | 358 (22.8) | 146 (16.9) | 89.3 (8.6) |
| 4 | 434 (20.2) | 212 (42.1) | 200 (38.8) | 93.6 (13.8) | 54.6 (2.84) |
| 6 | 432 (13.0) | 207 (80.6) | 136 (58.2) | 112 (15.1) | 55.7 (5.23) |
| 8 | 441 (37.3) | 189 (57.4) | 174 (49.2) | 113 (11.0) | 82.5 (12.3) |
| 10 | 519 (45.1) | 334 (57.0) | 219 (77.1) | 205 (48.1) | 61.9 (5.79) |
| 12 | 578 (14.6) | 515 (37.0) | 322 (80.7) | 245 (56.7) | 78.4 (8.52) |
| 18 | 544 (21.5) | 365 (49.6) | 237 (75.7) | 247 (80.6) | 65.0 (4.5) |
| 24 | 480 (16.4) | 237 (44.3) | 127 (34.3) | 116 (27.5) | 70.3 (8.49) |
| 36 | 593 (8.1) | 468 (80.6) | 367 (86.8) | 272 (70.6) | 104 (10.9) |
| 48 | 507 (19.7) | 332 (62.0) | 231 (61.6) | 131 (25.1) | 69.9 (10.1) |
| 60 | 601 (0) | 485 (78.9) | 407 (99.5) | 331 (49.4) | 122 (16.2) |
| 72 | 561 (8.02) | 365 (78.2) | 313 (72.8) | 188 (16.7) | 94.8 (5.96) |
| 84 | 598 (3) | 522 (67.3) | 466 (103.0) | 443 (39.9) | 190 (16.0) |
| 96 | 556 (13.3) | 435 (62.7) | 344 (77.6) | 306 (46.8) | 180 (28.7) |
| 108 | 600 (1.30) | 529 (68.7) | 598 (2.5) | 525 (45.7) | 349 (27.2) |
| 120 | 567 (19.9) | 497 (38.5) | 504 (13.5) | 408 (57.8) | 267 (30.8) |
| 120 hour AUC | 66682 (717) | 50061 (6354) | 42360 (6855) | 34185 (3632) | 17350 (767) |

*values above 601 are not measured because that is the high reading on the glucometer

TABLE 3B

Mean Pharmacokinetic Parameters of Example 1 in Male, STZ-treated, Sprague-Dawley Rats Following Single Subcutaneous Administrations of 50, 100, 200, or 400 nmol/kg of Example 1.

| | 50 nmol/kg Example 1 Mean ± SD | 100 nmol/kg Example 1 Mean ± SD | 200 nmol/kg Example 1 Mean ± SD | 400 nmol/kg Example 1 Mean ± SD |
|---|---|---|---|---|
| $T_{1/2}$ (hr) | 21 ± 1 | 21 ± 2 | 24 ± 1 | 20 ± 3 |
| Tmax (hr) | 16.8 ± 5.0 | 14.4 ± 5.4 | 10.8 ± 2.7 | 7.2 ± 2.7 |
| Cmax/D (kg*nM/nmol) | 6.77 ± 0.69 | 8.18 ± 1.13 | 8.35 ± 1.84 | 9.89 ± 1.91 |
| $AUC_{0\text{-}inf}$ (hr*μM) | 15.6 ± 1.03 | 38.0 ± 3.68 | 74.7 ± 9.57 | 185 ± 20.4 |
| CL/F (mL/hr/kg) | 3.29 ± 0.206 | 2.73 ± 0.282 | 2.80 ± 0.359 | 2.25 ± 0.285 |

TABLE 4A

Glucose-lowering of Example 2 in Male, STZ-treated, Sprague-Dawley Rats Following Single Subcutaneous Administrations of 50, 100, 200, or 400 nmol/kg of Example 2.

| Time (Hours) | Avg Glucose mg/dl (SEM) n = 5 Vehicle | Example 2 (50 nmol/kg) | Example 2 (100 nmol/kg) | Example 2 (200 nmol/kg) | Example 2 (400 nmol/kg) |
|---|---|---|---|---|---|
| 0 | 514 (24.9) | 506 (25.2) | 511 (25.0) | 554 (21) | 514 (27.8) |
| 1 | 522 (15.6) | 362 (38.4) | 377 (69.5) | 330 (46) | 225 (8.16) |
| 2 | 501 (9.42) | 186 (46.8) | 163 (36.7) | 140 (6) | 105 (24.2) |
| 4 | 431 (10.5) | 138 (13.7) | 142 (37.1) | 71 (10) | 88 (15.2) |
| 6 | 432 (20.5) | 139 (25.0) | 125 (30.8) | 191 (45) | 125 (22.4) |
| 8 | 488 (41.3) | 259 (73.9) | 185 (34.5) | 184 (69) | 121 (19.8) |
| 10 | 541 (28.3) | 380 (69.4) | 332 (55.2) | 280 (70) | 129 (7.58) |
| 12 | 601 (0.00) | 548 (24.7) | 493 (45.0) | 322 (78) | 175 (19.2) |
| 18 | 592 (7.74) | 513 (32.3) | 383 (52.1) | 173 (15) | 121 (8.99) |
| 24 | 499 (17.5) | 391 (51.7) | 285 (69.2) | 114 (18) | 103 (16.4) |
| 36 | 601 (0.40) | 572 (12.6) | 464 (56.9) | 187 (18) | 128 (20.0) |
| 48 | 552 (8.53) | 459 (31.6) | 333 (59.1) | 91 (10) | 82 (4.6) |
| 60 | 601 (0.00) | 584 (7.42) | 520 (43.7) | 249 (32) | 108 (12.4) |
| 72 | 527 (14.5) | 490 (11.3) | 376 (58.4) | 151 (30) | 60 (5.31) |
| 84 | 601 (0.00) | 601 (0) | 542 (39.7) | 433 (41) | 167 (20.2) |
| 96 | 531 (23.9) | 499 (15.3) | 402 (40.2) | 298 (69) | 86 (11.5) |
| 108 | 601 (0.00) | 600 (1.2) | 568 (22.4) | 516 (27) | 352 (31.2) |
| 120 | 552 (22.1) | 534 (27.6) | 487 (39.5) | 390 (42) | 197 (27.7) |
| 120 hour AUC | 67232 (536) | 60367 (1720) | 50661 (5087) | 31052 (2387) | 16886 (631) |

*values above 601 are not measured because that is the high reading on the glucometer

TABLE 4B

Mean Pharmacokinetic Parameters of Example 2 in Male, STZ-treated, Sprague-Dawley Rats Following Single Subcutaneous Administrations of 50, 100, 200, or 400 nmol/kg of Example 2.

| | 50 nmol/kg Example 2 Mean ± SD | 100 nmol/kg Example 2 Mean ± SD | 200 nmol/kg Example 2 Mean ± SD | 400 nmol/kg Example 2 Mean ± SD |
|---|---|---|---|---|
| $T_{1/2}$ (hr) | 16.1 ± 1.39 | 18.1 ± 2.17 | 21.3 ± 1.04 | 21.9 ± 3.62 |
| Tmax (hr) | 24.0 ± 7.3 | 19.2 ± 5.0 | 18.0 ± 4.2 | 14.4 ± 5.4 |
| Cmax/D (kg*nM/nmol) | 3.06 ± 0.56 | 4.69 ± 0.54 | 5.99 ± 0.77 | 6.2 ± 0.52 |

TABLE 4B-continued

Mean Pharmacokinetic Parameters of Example 2 in Male, STZ-treated, Sprague-Dawley Rats Following Single Subcutaneous Administrations of 50, 100, 200, or 400 nmol/kg of Example 2.

| | 50 nmol/kg Example 2 Mean ± SD | 100 nmol/kg Example 2 Mean ± SD | 200 nmol/kg Example 2 Mean ± SD | 400 nmol/kg Example 2 Mean ± SD |
|---|---|---|---|---|
| $AUC_{0\text{-}inf}$ (hr*μM) | 7.71 ± 1.1 | 23.8 ± 16.5 | 54.3 ± 3.91 | 119 ± 7.23 |
| CL/F (mL/hr/kg) | 6.69 ± 1.12 | 4.3 ± 0.33 | 3.82 ± 0.28 | 3.49 ± 0.24 |

TABLE 5A

Glucose-lowering of Example 3 in Male, STZ-treated, Sprague-Dawley Rats Following Single Subcutaneous Administrations of 50, 100, 200, or 400 nmol/kg of Example 3.

| Time (Hours) | Avg Glucose mg/dl (SEM) n = 5 Vehicle | Example 3 (50 nmol/kg) | Example 3 (100 nmol/kg) | Example 3 (200 nmol/kg) | Example 3 (400 nmol/kg) |
|---|---|---|---|---|---|
| 0 | 475 (19.8) | 486 (13.6) | 505 (23.3) | 534 (18.5) | 519 (32.3) |
| 1 | 475 (18.2) | 313 (17.7) | 413 (34.4) | 278 (21.3) | 301 (28.4) |
| 2 | 465 (22.4) | 122 (28.0) | 195 (56.0) | 116 (19.0) | 90 (9.52) |
| 4 | 444 (17.3) | 217 (60.5) | 162 (39.9) | 104 (20.9) | 98 (19.9) |
| 6 | 430 (18.0) | 179 (45.3) | 134 (26.3) | 175 (15.4) | 106 (22.0) |
| 8 | 452 (29.2) | 259 (71.2) | 247 (92.0) | 166 (37.6) | 99 (14.8) |
| 10 | 459 (44.0) | 394 (78.8) | 327 (100) | 172 (29.0) | 112 (19.3) |
| 12 | 569 (17.9) | 573 (11.4) | 494 (38.1) | 258 (55.6) | 153 (23.5) |
| 18 | 552 (16) | 469 (16.2) | 443 (39.6) | 166 (56.0) | 90 (7.40) |
| 24 | 467 (23.6) | 311 (68.3) | 188 (58.4) | 72 (6.17) | 71 (4.98) |
| 36 | 593 (3.70) | 528 (28.8) | 489 (29.8) | 154 (27.0) | 94 (13.0) |
| 48 | 507 (9.03) | 444 (19.6) | 257 (53.9) | 75 (9.77) | 47 (5.03) |
| 72 | 531 (19.6) | 475 (21.3) | 437 (15.4) | 114 (22.2) | 48 (2.42) |
| 84 | 579 (21.9) | 588 (7.61) | 560 (26.3) | 396 (22.8) | 112 (29.0) |
| 96 | 494 (7.31) | 472 (19.3) | 469 (23.0) | 288 (31.1) | 82 (12.6) |

TABLE 5A-continued

Glucose-lowering of Example 3 in Male, STZ-treated, Sprague-Dawley Rats Following Single Subcutaneous Administrations of 50, 100, 200, or 400 nmol/kg of Example 3.

| | Avg Glucose mg/dl (SEM) n = 5 | | | | |
|---|---|---|---|---|---|
| Time (Hours) | Vehicle | Example 3 (50 nmol/kg) | Example 3 (100 nmol/kg) | Example 3 (200 nmol/kg) | Example 3 (400 nmol/kg) |
| 108 | 578 (12.6) | 580 (10.3) | 584 (10.9) | 492 (16.5) | 405 (22.5) |
| 120 | 504 (5.09) | 486 (17.6) | 481 (18.5) | 369 (40.0) | 234 (26.6) |
| 120 hour AUC | 63389 (382) | 56237 (1523) | 49612 (2958) | 26200 (1092) | 14756 (404) |

*values above 601 are not measured because that is the high reading on the glucometer

TABLE 5B

Mean Pharmacokinetic Parameters of Example 3 in Male, STZ-treated, Sprague-Dawley Rats Following Single Subcutaneous Administrations of 50, 100, 200, or 400 nmol/kg of Example 3.

| | 50 nmol/kg Example 3 Mean ± SD | 100 nmol/kg Example 3 Mean ± SD | 200 nmol/kg Example 3 Mean ± SD | 400 nmol/kg Example 3 Mean ± SD |
|---|---|---|---|---|
| $T_{1/2}$ (hr) | 20 ± 2 | 19 ± 3 | 19 ± 3 | 20 ± 1 |
| Tmax (hr) | 25 ± 11 | 26 ± 5 | 24 ± 0 | 20 ± 3 |
| Cmax/D (kg*nM/nmol) | 4.89 ± 1.22 | 6.46 ± 1.32 | 6.17 ± 0.90 | 6.43 ± 0.41 |
| $AUC_{0-inf}$ (hr*μM) | 11.7 ± 2.8 | 33.9 ± 6.1 | 65.3 ± 6.3 | 143.0 ± 14.8 |
| CL/F (mL/hr/kg) | 4.50 ± 1.13 | 3.03 ± 0.56 | 3.09 ± 0.30 | 2.81 ± 0.28 |

Abbreviations for Tables 3B, 4B, 5B: $AUC_{0-inf}$=area under the curve from 0 to infinity, CL/F=clearance/bioavailability, Tmax=time to maximal concentration, Cmax/D=maximal plasma concentration per dose, $T_{1/2}$=half-life. [Data are mean+/−SD (N=5) The data in Tables 3A, 4A, and 5A show a robust dose-dependent glucose-lowering effect in vivo for all three examples. The data in Tables 3B, 4B, and 5B show sustained time of action in vivo for all three examples.

Evaluation of Drug Clearance in a Pig Model of Type 1 Diabetes

The purpose of this study is to investigate the glucose-lowering and pharmacokinetics of the Examples in diabetic Yucatan miniature swine following a single subcutaneous dose of 3.6 nmol/kg. Blood samples are collected over 168 hours post-dose.

Diabetic (alloxan induced), castrated, male Yucatan miniature swine (average age 23 months, average body weight of 44 kgs) are housed individually with ad libitum access to fresh water at all times and are fed two meals per day of house diet. Animals receive appropriate maintenance basal and prandial insulin twice per day to manage their diabetic condition when not on study. The animals are randomly placed into treatment groups and returned to their pens. Examples are formulated as 400 U/mL in a hexameric formulation (19 mg/mL glycerol, 4 Zn/hex, 3.15 mg/mL m-cresol, 10 mM Tris, pH 7.6)

The day prior to study, pigs are fed half their daily ration and receive 0.2 U/kg Humalog Mix 75/25 at their morning maintenance administration. Approximately 12 hours prior to the scheduled test dose administration, the pigs are fed half their daily ration and receive 0.2 U/kg of Humalog only. All animals remain fasted until after the 24 hour sample has been collected.

On the morning of study, all animals are placed into slings for restraint and have their vascular access ports accessed (equipped for blood sampling) and checked for patency. The animals are randomly placed into the treatment group (n=6) and returned to their individual pens. The first two pre-dose samples are collected, the animals are injected with test article 0.6 U/kg/3.6 nmol/Kg (based on the 400 U/ml insulin concentration, average of volume of 7 Units/pig) subcutaneously in the flank (0 min) with a U100 insulin syringe. All study animals have ad libitum access to clean, fresh water throughout the remaining blood collection period.

Serial blood samples (4.0 mL each) are collected from each animal and placed into tubes containing $K_3$EDTA anticoagulant at the following time points: −0.5, 0, 1.5, 3, 6, 12, 18, 24, 36, 42, 48, 54, 60, 72, 96, 120, 144, and 168 hours post subcutaneous (sc) dosing.

Animals are fed 300 grams of S-9 diet and administered 0.2 U/kg Humalog sc after the 24 and 60 hour samples. After the 72 hour samples, animals resume their normal maintenance insulin and feeding regimen. All samples are collected prior to morning food and maintenance insulin administration.

Whole blood samples are maintained on wet ice immediately following collection. Plasma is then separated by centrifugation (~3000 RPM at least 15 min at ~4° C.) and divided into two aliquots and stored frozen at approximately −20° C. for glucose analysis or −70° C. for PK analysis.

Plasma glucose concentrations are determined using an automated Beckman AU480 Clinical Chemistry Analyzer (Beckman Coulter, Brea, CA), and graphed with Graphpad Prism 8.

Immunoaffinity-LC/MS Pig Plasma Assay: To characterize the PK of test Example, plasma samples (100 μL aliquots) are analyzed for intact Example concentrations via immunoprecipitation followed by LC/MS analysis. Standards and blank samples are prepared in 100% control pig plasma using test Example, and a stable isotope-labeled antibody (unrelated to the Example) is added to all standards and samples as an internal standard. For immunoprecipitation, a biotin-labeled anti-human murine antibody (Fitzgerald, Catalog Number 10R-I134E) is used as a capture reagent, which is subsequently bound by Dynal M-280 streptavidin-coated magnetic beads (Invitrogen 60210). The magnetic bead-immobilized samples are washed with 0.1% CHAPS followed by PBS, and test Example and its internal standard are eluted with a solution containing 20% ACN, 2% aqueous formic acid, and 20% Invitrosol (Invitrogen, 46-5553). Plasma samples are quantified using a Thermo Q/Exactive Plus mass spectrometer over the range of 0.1 to 52.3 ng/mL (0.016 to 8.0 nM).

Pharmacokinetic Analysis: The non-compartmental pharmacokinetic analysis is conducted using Phoenix WinNonLin v8.1. For the PK analysis, the concentrations used in the estimation of the elimination half-life are averaged from 50 to 160 hours post-dose (corresponding to 3.6 nmol/kg SC).

TABLE 6A

| Glucose lowering data | | | |
|---|---|---|---|
| Time (Hours) | Example 1 Avg Glucose mg/dl (SEM) n = 6 | Example 2 Avg Glucose mg/dl (SEM) n = 5 | Example 3 Avg Glucose mg/dl (SEM) n = 7 |
| −0.5 | 443 (34) | 417 (35) | 373 (27) |
| 0 | 439 (36) | 410 (31) | 374 (27) |
| 1.5 | 436 (38) | 409 (33) | 361 (21) |
| 3 | 398 (27) | 364 (31) | 341 (23) |
| 6 | 311 (18) | 269 (46) | 250 (18) |
| 12 | 173 (25) | 176 (42) | 86 (15) |
| 18 | 124 (14) | 132 (30) | 69 (9) |
| 24 | 104 (13) | 110 (30) | 50 (4) |
| 36 | 146 (24) | 208 (22) | 128 (28) |
| 42 | 246 (33) | 268 (5) | 185 (40) |
| 48 | 206 (32) | 236 (25) | 126 (29) |
| 54 | 136 (38) | 159 (33) | 72 (9) |
| 60 | 127 (36) | 148 (30) | 77 (9) |
| 72 | 194 (45) | 205 (39) | 110 (27) |
| 96 | 296 (36) | 293 (36) | 247 (22) |
| 120 | 311 (30) | 319 (16) | 226 (51) |
| 144 | 264 (20) | 276 (23) | 194 (26) |
| 168 | 143 (45) | 233 (41) | 196 (46) |

TABLE 6B

| Mean PK Parameters of Examples 1, 2, 3 in Male Diabetic-Induced Yucatan Swine Following Single Subcutaneous Doses. | | | |
|---|---|---|---|
| | 3.6 nmol/kg Example 1 Mean ± SD | 3.6 nmol/kg Example 2 Mean ± SD | 3.6 nmol/kg Example 3 Mean ± SD |
| $T_{1/2}$ (hr) | 45 ± 11 | 39 ± 5 | 39 ± 10 |
| Tmax (hr) | 15 ± 7 | 13 ± 7 | 15 ± 5 |
| Cmax (pmol/L) | 25.8 ± 2.20 | 19.5 ± 4.68 | 21.1 ± 2.99 |
| $AUC_{0-inf}$ (hr* nmol/L) | 2.11 ± 0.300 | 1.26 ± 0.156 | 1.46 ± 0.193 |
| CL/F (mL/hr/kg) | 1.74 ± 0.23 | 2.88 ± 0.34 | 2.50 ± 0.33 |

Abbreviations:
$T_{1/2}$ = half-life,
$T_{max}$ = time to maximal concentration,
$C_{max}$ = maximal plasma concentration,
$AUC_{0-inf}$ = area under the curve from 0 to infinity,
CL/F = clearance/bioavailability (N = 6 for test Example)

The data in Tables 6A and 6B show a robust and protracted glucose-lowering effect in vivo for all three examples in the pig model of Type 1 Diabetes.

Sequences

Modified Insulin A-Chain (A14E); A-Chain of Formula 1
SEQ ID NO: 1
GIVEQCCTSICSLEQLENYCN Modified Insulin B-Chain (B16H, B25H, desB30); B-Chain of Formula 1
SEQ ID NO: 2
FVNQHLCGSHLVEALHLVCGERGFHYTPK Wherein Lys at position 29 is chemically modified by conjugation of the epsilon-amino group of the Lys side-chain with $HO_2C—(CH_2)_{18}—CO$-γGlu-γGlu-γGlu-X—, wherein X is -Lys-Gly-, -Lys-(2-[2-(2-aminoethoxy)ethoxy]acetic acid)-, or -εLys-Gly-.

B-Chain of Example 1
SEQ ID NO: 3
FVNQHLCGSHLVEALHLVCGERGFHYTPK

Wherein Lys at position 29 is chemically modified by conjugation of the epsilon-amino group of the Lys side-chain with $HO_2C—(CH_2)_{18}—CO$-γGlu-γGlu-γGlu-Lys-Gly-.

B-Chain of Example 2
SEQ ID NO: 4
FVNQHLCGSHLVEALHLVCGERGFHYTPK

Wherein Lys at position 29 is chemically modified by conjugation of the epsilon-amino group of the Lys side-chain with $HO_2C—(CH_2)_{18}—CO$-γGlu-γGlu-γGlu-Lys-(2-[2-(2-aminoethoxy)ethoxy]acetic acid)-.

B-Chain of Example 3
SEQ ID NO: 5
FVNQHLCGSHLVEALHLVCGERGFHYTPK

Wherein Lys at position 29 is chemically modified by conjugation of the epsilon-amino group of the Lys side-chain with $HO_2C—(CH_2)_{18}—CO$-γGlu-γGlu-γGlu-εLys-Gly-.

C-terminal C9 epitope
SEQ ID NO: 6
TETSQVAPA

Single Chain Insulin
SEQ ID NO: 7
MHHHHHHQAIFVLQGSLDQDPEFENLYFQI

EGGRFVNQHLCGSHLVEALHLVCGERGFHY

TPKRREAEDLQVGQVELGGGPGAGSLQPLA

LEGSLQRGIVEQCCTSICSLEQLENYCN

Modified Insulin B-Chain (B16H, B25H, desB30)
SEQ ID NO: 8
FVNQHLCGSHLVEALHLVCGERGFHYTPK

We claim:

1. A compound of Formula I:

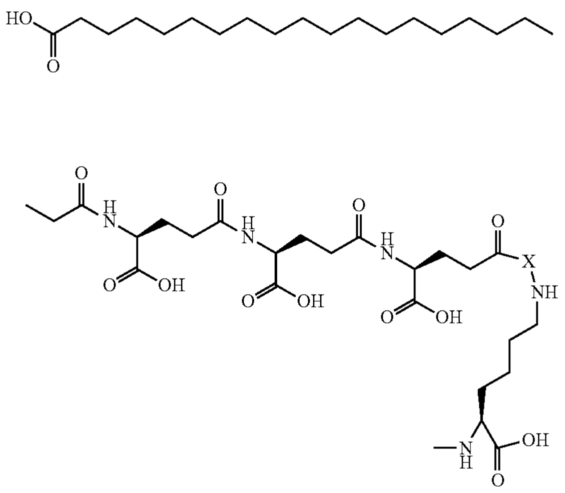

-continued

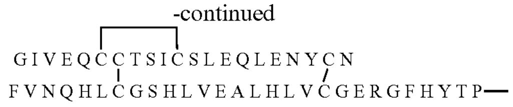

wherein X is selected from the group consisting of -Lys-Gly-, -Lys-(2-[2-(2-aminoethoxy)ethoxy]acetic acid)-, and -εLys-Gly-; or a pharmaceutically acceptable salt thereof.

2. The compound of claim 1 wherein X is -Lys-Gly-, or a pharmaceutically acceptable salt thereof.

3. The compound of claim 1 wherein X is -Lys-(2-[2-(2-aminoethoxy)ethoxy]acetic acid)-, or a pharmaceutically acceptable salt thereof.

4. The compound of claim 1 wherein X is -εLys-Gly-, or a pharmaceutically acceptable salt thereof.

5. The compound of claim 1 that is

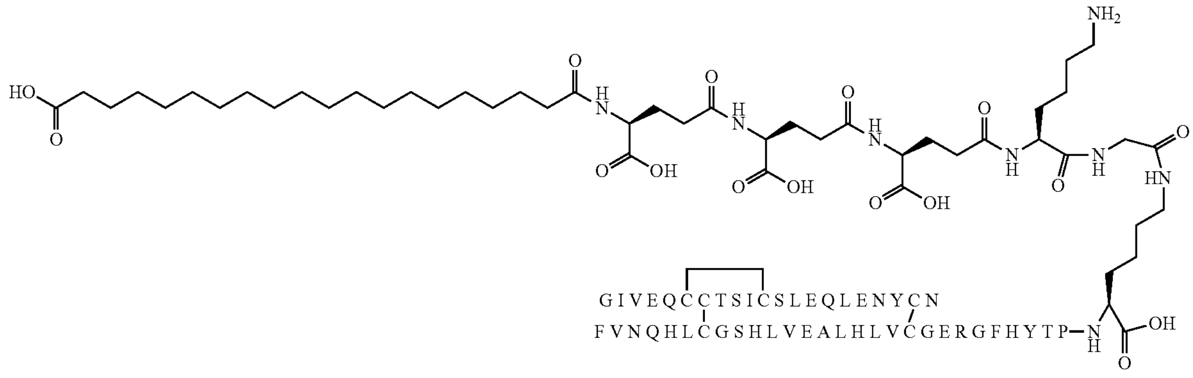

or a pharmaceutically acceptable salt thereof.

6. The compound of claim 1 that is

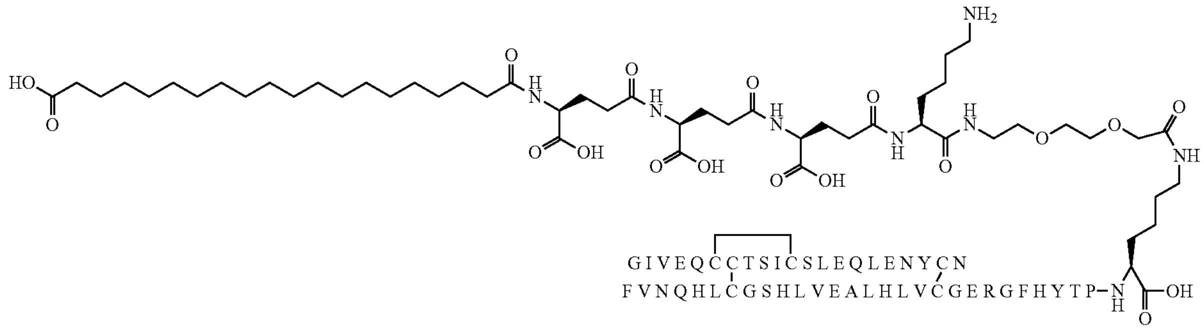

or a pharmaceutically acceptable salt thereof.

7. The compound of claim 1 that is

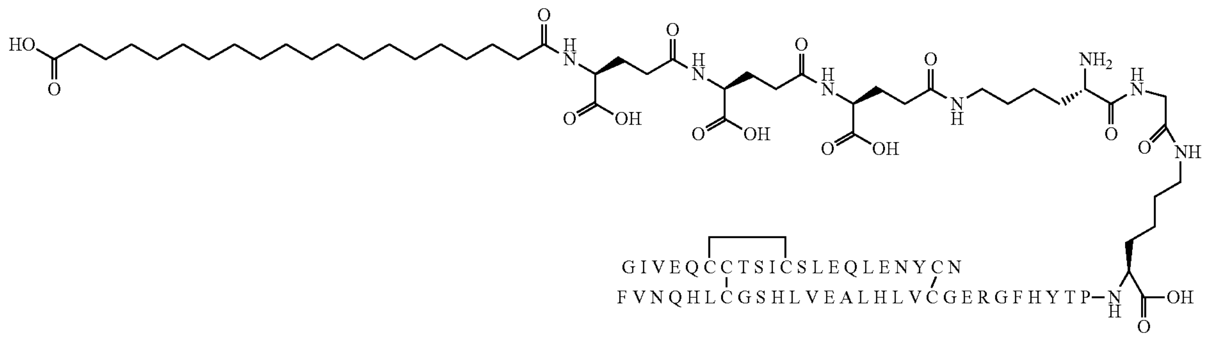

or a pharmaceutically acceptable salt thereof.

8. A pharmaceutical composition comprising a compound of claim 1 or a pharmaceutically acceptable salt thereof, and one or more pharmaceutically acceptable excipients.

9. A method of treating Type I and/or Type II diabetes in a patient comprising administering to a patient in need thereof an effective amount of a compound of claim 1 or a pharmaceutically acceptable salt thereof, or the pharmaceutical composition of claim 8.

10. A method of treating hyperglycemia in a patient comprising administering to a patient in need thereof an effective amount of a compound of claim 1 or a pharmaceutically acceptable salt thereof, or the pharmaceutical composition of claim 8.

11. The compound of claim 1 or a pharmaceutically acceptable salt thereof, for use in therapy.

12. The compound of claim 1 or a pharmaceutically acceptable salt thereof, for use in the treatment of Type I and/or Type II diabetes.

13. The compound of claim 1 or a pharmaceutically acceptable salt thereof, for use in the treatment of hyperglycemia.

* * * * *